United States Patent [19]

Bandyopadhyay et al.

[11] Patent Number: 5,871,956
[45] Date of Patent: Feb. 16, 1999

[54] RECOMBINANT METHODS FOR PRODUCTION OF SERINE INHIBITORS AND DNA SEQUENCES USEFUL FOR SAME

[75] Inventors: Pradip K. Bandyopadhyay; Stephen P. Eisenberg, both of Boulder; Gary L. Stetler, Lafayette; Robert C. Thompson, Boulder, all of Colo.

[73] Assignee: Amgen Inc., Thousand Oaks, Calif.

[21] Appl. No.: 279,056

[22] Filed: Jul. 22, 1994

Related U.S. Application Data

[63] Continuation of Ser. No. 563,832, Aug. 6, 1990, abandoned, which is a continuation of Ser. No. 31,846, Mar. 30, 1987, abandoned, which is a continuation-in-part of Ser. No. 890,526, Jul. 29, 1986, abandoned, which is a continuation-in-part of Ser. No. 903,471, Sep. 3, 1986, abandoned, which is a continuation-in-part of Ser. No. 678,822, Dec. 5, 1984, abandoned.

[51] Int. Cl.⁶ .......................... C12N 15/15; C12N 15/70; C12N 15/75; C12N 15/81
[52] U.S. Cl. ................. 435/69.1; 435/172.3; 435/252.3; 435/252.31; 435/252.33; 435/254.21; 435/320.1; 536/23.5; 930/250; 930/260; 935/10; 935/69; 935/73; 935/74
[58] Field of Search ............................... 435/69.1, 172.3, 435/252.3, 320.1, 252.33, 254, 252.31, 254.21, 23.5; 536/23.5

[56] References Cited

U.S. PATENT DOCUMENTS

| | | | |
|---|---|---|---|
| 4,394,443 | 7/1983 | Weissman et al. | 435/6 |
| 4,511,503 | 4/1985 | Olson et al. | 435/172.3 |
| 4,530,901 | 7/1985 | Weissman | 435/70 |
| 4,546,082 | 10/1985 | Kurjan et al. | 435/172.3 |
| 4,595,674 | 6/1986 | Tschesche et al. | 514/9 |
| 4,626,510 | 12/1986 | Girandi | 435/312 |
| 4,652,639 | 3/1987 | Stabinsky | 536/27 |
| 4,672,032 | 6/1987 | Slavkin et al. | 435/68 |
| 4,711,848 | 12/1987 | Insley et al. | 435/91 |
| 4,720,454 | 1/1988 | White et al. | 435/6 |
| 4,760,130 | 7/1988 | Thompson et al. | 530/350 |
| 4,788,135 | 11/1988 | Davis et al. | 435/6 |
| 4,845,076 | 7/1989 | Heinzel et al. | 514/12 |
| 4,923,807 | 5/1990 | Webb et al. | 435/69.2 |
| 4,952,512 | 8/1990 | Loskutoff et al. | |
| 5,102,995 | 4/1992 | Tollefsen et al. | 536/23.1 |
| 5,109,113 | 4/1992 | Caras et al. | 530/350 |
| 5,151,438 | 9/1992 | Sham et al. | 514/357 |
| 5,157,019 | 10/1992 | Glover et al. | 514/12 |
| 5,215,915 | 6/1993 | Tiberi et al. | 435/252.3 |
| 5,252,725 | 10/1993 | Rubin et al. | 536/23.5 |
| 5,376,633 | 12/1994 | Lezdey et al. | 514/8 |
| 5,532,215 | 7/1996 | Lezdey et al. | 514/8 |

FOREIGN PATENT DOCUMENTS

| | | |
|---|---|---|
| 114 506 | 8/1984 | European Pat. Off. . |
| 0 346 500B1 | 7/1994 | European Pat. Off. . |
| 84 03 711 | 9/1984 | WIPO . |
| 86 03 497 | 6/1986 | WIPO . |
| 86 03 519 | 6/1986 | WIPO . |

OTHER PUBLICATIONS

Alberts, B., et al. (1983), "Recombinant DNA Technology," *Molecular Biology of the Cell*, Garland Publishing, Inc., New York, pp. 185–196.

Anon (1994), "Aids drugs: Beyond access," The Economist of January 8th 1994, p. 79.

(List continued on next page.)

*Primary Examiner*—Robert Wax
*Assistant Examiner*—William W. Moore
*Attorney, Agent, or Firm*—Finnegan, Henderson, Farabow, Garrett & Dunner

[57] ABSTRACT

A synthetic DNA sequence and its genetic equivalents are disclosed which sequences are capable, when used in a recombinant DNA method, of directing production of a serine protease inibitor protein. Recombinant DNA methods for the production of serine protease inhibitor proteins are also disclosed. These methods incorporate either the synthetic DNA sequence of the present invention or natural DNA sequences isolated from human cDNA or genomic libraries.

23 Claims, 6 Drawing Sheets

OTHER PUBLICATIONS

Rice et al., "Regulation of Proteolysis at the Neutrophil–Substrate Interface by Secretory Leukoprotease Inhibitor," *Science,* 249:178–181 (1990).

Ohlsson et al. (1984), "Localization of antileukoprotease in the parotid and the submandibular salivary glands," *Biological Abstracts,* 78:ref. No. 90008 and Acta Otolaryngol (Stockh) (1984), 98:147–151.

Eisenberg, S.P., et al., "Location of the Protease–inhibitory Region of Secretory Leukocyte Protease Inhibitor," *The Journal of Biological Chemistry,* 265:7976–7981 (1990).

Lucey et al. (1990), "Recombinant human secretory leukocyte–protease inhibitor: In vitro properties, and amelioration of human neutrophil elastase–induced emphysema and secretory cell metaplasia in the hamster," *J. Lob. Clin. Med.,* 115/2:224–232.

Birrer et al. (1992), "Intravenous recombinant secretory leukoprotease inhibitor augments antineutrophil elastase defense," *Journal of Applied Physiology,* 73/1:317–323.

Ohlsson et al. (1986), "Structure, Genomic Organization, and Tissue Distribution of Human Secretory Leukocyte–Protease Inhibitor (SLPI): A Potent Inhibitor of Neutrophil Elastase," *Pulmonary Emphysema and Proteolysis,* Academic Press, Inc., pp. 307–324.

Darnell et al. (1986), "Molecular Cell Biology," *Scientific American Books, Inc.,* pp. 54–55 and 258–260.

Wong, Y. N., et al. (1994), "A pharmakointeic evaluation of HIV protease inhibitors, cyclic ureas, in rats and dogs," *Biopharmacuetics & Drug Disposition,* 15:535–544.

Dorsey, B. D., et al. (1994), "Synthesis and evaluation of pyridyl analogs of L–735,524: Potent HIV–1 portease inhibitors," *Bioorganic Medicinal Chemistry Letters,* 4:2769–2774.

Rose, J. R., et al. (1994), "Structure–assisted design of nonpeptide human immunodeficiency virus–1 protease inhibitors," *American Journal of Respiratory and Critical Care Medicine,* 150:S176–S182.

Chen, Z., et al. (1995), "Three–dimensional structure of a mutant HIV–1 protease displaying cross–resistance to all protease inhibitors in clinical trials," *The Journal of Biological Chemistry,* 270:21433–21436.

Maschera, B., et al. (1995), "Analysis of resistance to human immunodeficiency virus type—protease inhibitors by using matched bacterial expression and proviral infection vectors," *Journal of Virology,* 69:5431–5436.

Kramps et al. (1990), "Proteinase inhibitor activities of antileukoprotease are represented by its second COOH–terminal domain," *Biochimca et Biophysica Acta,* 1038/2:178–185.

Böhm et al. (1991), "Purification of a serine–proteinase inhibitor from human articular cartilage," *Biochem. J.,* 274:269–273.

Hirsch, M. S. (1988), "Antiviral Drug Development for the Treatment of Human Immunodeficiency Virus Infections," *The American Journal of Medicine,* 85:182–185.

Creighton, T. E. (1983), "Proteins: Structures and Molecular Principles," Freeman & Company, NY, pp. 93–94.

Amann et al. (1983), "Vectors bearing a hybrid trp–lac promoter userful for regulated expression of cloned genes in *Escherchia coli,*" *Gene,* 25:167–178.

Anderson et al. (1983), "Isolation of a genomic clone for bovine pancreatic trypsin inhibitor by using a unique–sequence synthetic DNA probe," *Proc. Natl. Acad. Sci. USA,* 80:6838–6842.

Botstein et al. (1982), "Principles and Practice of Recombinant DNA Research with Yeast," *The Molecular Biology of the Yeast Sacchromyces,* 607–636.

Brake et al. (1984), "α–Factor–directed synthesis and secretion of mature foreign proteins in *Saccharomyces cerevisiae,*" *Proc. Natl. Acad. Sci. USA,* 81:4642–4646.

Fritz (1988), "Human Mucus Proteinase Inhibitor (Human MPI)," *Biol. Chem. Hoppe–Seyler,* 369:79–82.

Fritz (1980), "Proteinase inhibitors in severe inflammatory processes (septic shock and experimental endotoxaemia): biochemical, pathophysiological and therapeutic aspects," *Protein Degradation in Health and Disease, Ciba Foundation Symposium,* 75:351–379.

Ghrayeb et al. (1984), "Secretion cloning vectors in *Escherichia coli,*" *The EMBO J.,* 3:2437–2442.

Kueppers (1971), "Proteinase Inhibitor in Human Tears," *Biochem. Biophys. Acta,* 229:845–849.

Leicht et al. (1982), "Sequence homology and structural comparison between the chromosomal human $a_1$–antitrypsin and chicken ovalbumin genes," *Nature,* 297:655–659.

Miller et al. (1981), "Synthesis of Biologically Active Proteins by Recombinant DNA Technology," *Drug Development Research,* 1:435–454.

Ohlsson et al. (1977), "Isolation and Partial Characterization of a Low Molecular Weight Acid Stable Protease Inhibitor from Human Bronchial Secretion," *Hoppe–Seyler's Z. Physiol. Chem.,* 358:583–589.

Schiessler et al., (1976), "Inhibitors of Acrosin and Granulocyte Proteinase from Human Genital Tract Secretions," *Hoppe–Seyler's Z. Physiol. Chem. Bd.,* 357:1251–1260.

Schiessler et al. (1978), "Acid–stable inhibitors of granulocyte neutral proteases in human mucous secretions: biochemistry and possible biological function," *Chemical Abstracts,* 89:abtr. No. 192866u and Neutral Protease of Human Polymorphonuclear Leukocytes, Urban & Schwarzenberg, Inc. Baltimore—Munich, pp. 195–207 (1978).

Travis et al. (1983), "Human Plasma Proteinase Inhibitors," *Ann. Rev. Biochem.,* 52:655–709.

Wallner et al. (1974), "Characterization of an Acid–Stable Proteinase Inhibitor in Human Cervical Mucus," *Hoppe–Seyler's Z. Physiol. Chem. Bd.,* 355:709–715.

Stetler et al. (1989), "Secretion of Active, Full–and Half–[] Human Secretory Leukocyte Protease Inhibitor by Saccharomyces Cerevisiae," *Bio/Technology,* 7(1):55–60.

Smith et al. (1985), "Human bronchial leucocyte proteinase inhibitor," *Biochem. Journal,* 225:463–472.

Whitson, et al. (1986), "Dissociation of the Lactose Repressor—Operator DNA Complex: Effects of Size and Sequence Context of Operator–Containing DNA," *Biochemistry,* 25:3845–3852.

Chang, et al. (1986), "*Saccharomyces cerevisiae* Secretes and Correctly Processes Human Interferon Hybrid Proteins Containing Yeast Invertase Signal Peptides," *Molecular and Cellular Biology,* 6:1812–1819.

Julius et al. (1984), "Isolation of the Putative Structural Gene for the Lysine–Arginine–Cleaving Endopeptidase Required for Processing of Yeast Prepro–α –Factor,3" *Cell,* 37:1075–1089.

Broach, James R. (1983), "Construction of High Copy Yeast Vectors Using 2 μm Circle Sequences," *Methods in Enzymology,* 101:307–325.

Emr et al. (1983), "An MFα1–SUC2 (α–factor–invertase) gene fusion for study of protein localization and gene expression in yeast," *Proc. Natl. Acad. Sci. USA*, 80:7080–7084.

Derynck et al. (1984), "Human Transforming Growth Factor–α: Precursor Structure and Expression in E. coli," *Cell*, 38:287–297.

Van Arsdell et al. (1987), "The Yeast Repeated Element Sigma Contains a Hormone–Inducible Promoter," *Molecular and Cellular Biology*, 7/2:749–759.

Kurjan et al. (1982), "Structure for a Yeast Pheromone Gene (Mfα): A Putative α–Factor Precursor Contains Four Tandem Copies of Mature α–Factor," *Cell*, 30:933–943.

Swift et al. (1982), "Rat pancreatic kallikrein mRNA: Nucleotide sequence and amino acid sequence of the encoded preproenzyme," *Proc. Natl. Acad.Sci. USA*, 79:7263–7267.

Seto et al., *Chemical Abstracts*, vol. 100, (1984), No. 46033z.

Ballou et al., *Chemical Abstracts*, vol. 97, (1982), No. 51668j.

Jonassen et al., *Chemica Abstracts*, vol. 95, (1981), No. 2484w.

Chandrasekar, *Chemical Abstracts*, vol. 95, (1981), No. 169751.

Bernon et al., *Chemical Abstracts*, vol. 84, (1975), No. 28236.

Ohlsson et al., *Chemical Abstracts*, vol. 99, (1983), No. 173443.

Wengenmayer, F. (1983), "Synthesis of Peptide Hormones Using Recombinant DNA Techniques," *Agnew. Chem. Int. Ed. Engl.* 22, pp. 842–858.

Schiessler et al. (1977), "The Acid–stable Proteinase Inhibitor (Antileukoprotease) of Human Cervical Mucus," *The Uterine Cervix in Reproduction Workshop Conference Rottach–Egern, Georg Thieme Stuttgart*, pp. 84–89.

Schiessler et al. (1978), "Inhibitors of Granolocyte Proteases (Antileukoprotease) in Human Genital Tract Secretions," *Human Fertilization International Workshop Essen*, Jul. 1976, Georg Thieme Publishers Stuttgart, pp. 101–106.

Roberts, et al. (1983), "Recombinant DNA Technology," *Molecular Biology of The Cell*, 185–196.

Rogers, J. et al, *Biochem Biophys Res Comm*, vol. 116, pp. 375–382, 1983.

Ohlsson, M. et al, *Hoppe–Seyler's Z. Physiol. Chem.*, vol. 364, pp. 1323–1328, 1983.

Kurachi, K. et al, *Proc. Natl. Acad Sci*, vol. 78, pp. 6826–6830, 1981.

Valeuzuela, P. et al, *Nature*, vol. 298, pp. 347–350, 1982.

Lovett, P et al in Methods in Enzymology, vol. 68, pp. 342–357, 1979.

Stetler, et al, *Nuc Acids Rese*, vol. 14, pp. 7883–7896, 1986.

Fritz et al, *Agents & Actions*, vol. 8, 1–2, pp. 57–64, 1978.

Semuller et al, *FEBS Letters*, vol. 199, 1, pp. 43–48, 1986.

Hewick, R.M., et al, 1981, The Journal of Biological Chemistry 256(15):7990–7997.

Maniatis, T., et al., 1982, *Molecular Cloning, A Laboratory Manual*, Cold Spring Harbor Laboratory Press, pp. 190–193, 232.

Young, R.A., et al., 1983, Proceedings, National Academy of Sciences USA, 80:1194–1197.

Helfman, P.M., et al., 1983, Proceedings, National Academy of Sciences USA, 80: 31–35.

Leytas, S.P., et al., 1984, Proceedings, National Academy of Sciences USA, 81: 3699–3702.

Landau, N.R., et al., 1984, Proceedings, National Academy of Sciences USA 81: 5836–5840.

Thompson, R.C., and Ohlsson, K., 1986, Proceedings of the National Academy of Sciences, U.S.A., 83:6692–6696.

Klasen, E.C., and Kramps, J.A., 1985, Biochemical and Biophysical Research Communications, 128:285–289.

Morra, N.R., 1980, Journal of Molecular Biology, 143:317–328.

DERIVED FROM pGS185
WITH THE EcoR₁ FRAGEMENT
CONTAINING THE ∝-FACTOR
GENE FROM pCY17

VECTOR:
   COMPLETE 2μ
   LEU 2d
   URA 3
   AMP$^r$

PROMOTER:
   S. CEREVISIAE SIGMA ELEMENT
   POSITIVELY REGULATED BY MATING FACTORS

SECRETION SIGNAL:
   SYNTHETIC SUC2 LEADER pΣ-1A pUC 18 CONTAINING THE SST I-XhoIB FRAGMENT OF SIGMA ISOLATED FROM pGS75

RECOMBINANT METHODS FOR PRODUCTION OF SERINE INHIBITORS AND DNA SEQUENCES USEFUL FOR SAME

This application is a continuation of application Ser. No. 07/563,832, filed Aug. 6, 1990, now abandoned, which is a continuation of application Ser. No. 07/031,846 filed Mar. 30, 1987, now abandoned, which is a continuation-in-part of U.S. patent application Ser. No. 06/890,526, filed Jul. 29, 1986, now abandoned, which is a continuation-in-part of U.S. patent application Ser. No. 06/903,471, filed Sep. 3, 1986, now abandoned, which is a continuation-in-part of U.S. patent application Ser. No. 678,822, filed Dec. 5, 1984, and now abandoned.

BACKGROUND OF THE INVENTION

Endogenous proteolytic enzymes serve to degrade invading organisms, antigen-antibody complexes and certain tissue proteins which are no longer necessary or useful to the organism. In a normally functioning organism, proteolytic enzymes are produced in a limited quantity and are regulated in part through the synthesis of protease inhibitors.

A large number of naturally-occurring protease inhibitors serve to control the endogenous proteases by limiting their reactions locally and temporally. In addition, the protease inhibitors may inhibit proteases introduced into the body by infective and parasitic agents. Tissues that are particularly prone to proteolytic attack and infection, e.g., those of the respiratory tract, are rich in protease inhibitors.

Protease inhibitors comprise approximately 10% of the human plasma proteins. At least eight inhibitors have been isolated from this source and characterized in the literature. These include $\alpha_2$-macroglobulin ($\alpha_2$M), $\alpha_1$-protease inhibitor ($\alpha_1$PI), $\alpha_1$-antichymotrypsin ($\alpha_1$Achy), $\beta_1$-anticollagenase ($\beta_1$AC), and inter-$\alpha$-trypsin inhibitor (I$\alpha$I).

A disturbance of the protease/protease inhibitor balance can lead to protease mediated tissue destruction, including emphysema, arthritis, glomerulonephritis, periodontitis, muscular dystrophy, tumor invasion and various other pathological conditions. In certain situations, e.g., severe pathological processes such as sepsis or acute leukemia, the amount of free proteolytic enzymes present increases due to the release of enzyme from the secretory cells. In addition, or separately in other situations, a diminished regulating inhibitor capacity of the organism may also cause alterations in the protease/protease inhibitor balance. An example of such a diminished regulating inhibitor capacity is $\alpha_1$-protease inhibitor deficiency, which is highly correlated with the development of pulmonary emphysema.

In organisms where such aberrant conditions are present, serious damage to the organism can occur unless measures can be taken to control the proteolytic enzymes. Therefore, protease inhibitors have been sought which are capable of being administered to an organism to control the proteolytic enzymes.

Leukocyte elastase is an example of a serine protease of particular interest from a pharmacological standpoint. Leukocyte elastase, when released extracellularly, degrades connective tissue and other valuable proteins. While it is necessary for a normally functioning organism to degrade a certain amount of connective tissue and other proteins, the presence of an excessive amount of leukocyte elastase has been associated with various pathological states, such as emphysema and rheumatoid arthritis. To counteract the effects of leukocyte elastase when it is present in amounts greater than normal, a protease inhibitor has been sought which is effective against leukocyte elastase. Such a protease inhibitor would be especially useful if it were capable of being prepared, via a recombinant DNA method, in a purified form and in sufficient quantities to be pharmaceutically useful.

In the past, at least two leukocyte elastase inhibitors have been identified in the literature. One protein, described in Schiessler et al., "Acid-Stable Inhibitors of Granulocyte Neutral Proteases in Human Mucous Secretions: Biochemistry and Possible Biological Function," in Neutral Proteases of Human Polymorphoneuclear Leucocytes, Havemann et al. (eds), Urban and Schwarzenberg, Inc. (1978), was isolated from human seminal plasma and sputum and was characterized as being approximately 11 Kda in size with tyrosine as the N-terminal amino acid. The literature reports of this protein have only furnished a partial amino acid sequence, but even this partial sequence indicates that this protein varies substantially from the proteins of the present invention. The reports of the sequence of this protein, in combination with amino acid sequence data for proteins of the present invention, indicate to the present inventors that the product sequenced by Schiessler et al. may have been a degraded protein which was not a single-polypeptide chain.

A second protein, isolated in one instance from human plasma, has been named $\alpha_1$-protease inhibitor. Work on this protein has been summarized in a review by Travis and Salvesen, Annual Review of Biochemistry 52: 655–709 (1983). The reports of the amino acid sequence of this protein indicate that it too differs substantially from the proteins of the present invention.

Because of the substantial differences in structure between single-polypeptide-chain proteins of the present invention and any single-polypeptide-chain serine protease inhibitors of the prior art, the single-polypeptide-chain serine protease inhibitors of the prior art are not "substantially homologous" to the proteins of the present invention.

Trypsin is another protease of particular interest from a pharmacological standpoint. Trypsin is known to initiate degradation of certain soft organ tissue, such as pancreatic tissue, during a variety of acute conditions, such as pancreatitis. Various efforts have been directed toward the treatment of these conditions, without marked success, through the use of proteins which it was hoped would inhibit the action of trypsin. Illustrative of such efforts are attempts to use exogenous bovine trypsin inhibitors in treatment of human pancreatitis. While such techniques have been attempted in Europe, they have not been approved as effective by the U.S. Food and Drug Administration. Thus, there is a need for a protease inhibitor effective in neutralizing excess trypsin in a variety of acute and chronic conditions. As was the case with the leukocyte elastase inhibitor discussed above, a trypsin inhibitor would be particularly useful if it could be isolated and prepared, by recombinant DNA methods, in a purified form and in sufficient quantities to be pharmaceutically useful.

Cathepsin G is another protease present in large quantities in leukocytes. Cathepsin G is known to be capable of degrading in vitro a variety of valuable proteins, including those of the complement pathway. Pancreatic elastase is another protease which may have a role in pancreatitis. Thus, inhibitors for these proteases are also of potential pharmaceutical value.

Leukocyte elastase, trypsin, cathepsin G and pancreatic elastase are examples of a class of proteases known as serine proteases, which have elements of common structure and mechanism. Their activity against different substrates and their sensitivity to different inhibitors are believed to result from changes in only a few amino acid residues. By analogy, it is possible to conceive of a class of serine protease inhibitors, also having common elements of structure and mechanism, in which changes in a relatively few amino acids will result in inhibition of different proteases, and that at least one member of this class will inhibit every serine protease of the former class. The class of serine protease inhibitors would then be of substantial value.

Surprisingly, the present inventors have discovered a DNA sequence capable of directing synthesis of such a serine protease inhibitor, which inhibitor is biologically equivalent to one isolated from parotid secretions. The protease inhibitor of the present invention, prepared by the recombinant DNA methods set forth herein, is believed to have at least two active sites; one site which exhibits leukocyte elastase inhibiting properties and a second site which exhibits inhibitory activity against trypsin.

The recombinant inhibitor produced by the present invention is believed to be remarkably resistant to denaturation by heat and acids and resistant to proteolytic degradation by a variety of proteolytic enzymes. As used in this application, it is intended that "recombinant inhibitor" refer to a protease inhibitor which is produced by recombinant DNA methodology and techniques. Furthermore, the active form of the recombinant inhibitor of the present invention is thermodynamically stable under conditions that are normally encountered extracellularly in the mammalian body. Denatured forms of the recombinant protease inhibitor also have the ability to form the disulfide bonds and to form the noncovalent interactions necessary to assume an active tertiary structure in the absence of biochemical stimulus.

The DNA sequences of the present invention, set forth more fully hereinbelow, are capable of directing synthesis of a protein which differs greatly from other published leukocyte elastase inhibitor sequences. Thus, the identification of the DNA sequence of the present invention has made possible the invention of recombinant DNA methods of manufacturing the novel recombinant protease inhibitors disclosed herein.

Such recombinant methods will allow manufacture of the inhibitors in quantities and purities sufficient to provide economical pharmaceutical compositions which possess serine protease inhibitory activity. Moreover, the identification of the DNA sequence has made possible the invention of recombinant DNA methods of manufacturing analogs of the above described serine protease inhibitor.

SUMMARY OF THE INVENTION

This invention relates to recombinant DNA methods for the manufacture of protease inhibitors generally and, more specifically, to the manufacture of recombinant inhibitors directed to human polymorphonuclear (PMN)-granulocyte proteases. In particular, this invention relates to recombinant DNA methods for the manufacture of inhibitors for human serine proteases, including leukoctye elastase and trypsin.

Additionally, the present invention relates to recombinant DNA methods for the manufacture of analogs of the instant serine protease inhibitors. The present invention also relates to synthetic and natural DNA sequences useful in the recombinant DNA methods as set forth below.

It is an object of the present invention to provide a method for recombinant DNA synthesis of a serine protease inhibitor, which inhibitor is a single polypeptide chain that exhibits serine protease inhibitor activity. These inhibitors possess activity which is biologically equivalent to that activity exhibited by native leukocyte elastase or trypsin inhibitors isolated from human parotid secretions.

To facilitate alternative recombinant DNA syntheses of these serine protease inhibitors, it is a further object of this invention to provide synthetic DNA sequences capable of directing production of these recombinant protease inhibitors, as well as equivalent natural DNA sequences. Such natural DNA sequences may be isolated from a cDNA or genomic library from which the gene capable of directing synthesis of the protease inhibitor may be identified and isolated.

Moreover, it is an object of the present invention to provide recombinant DNA methods for the manufacture of analogs of the protease inhibitors discussed above and corresponding analogous DNA sequences useful in such methods.

Additional objects and advantages of the invention will be set forth in part in the description which follows, and in part will be obvious from the description or may be learned from practice of the invention. The objects and advantages may be realized and attained by means of the instrumentalities and combinations particularly pointed out in the appended claims.

To achieve the objects and in accordance with the purposes of the present invention, a DNA sequence has been discovered which is capable of directing the production, by recombinant DNA methodology, of protease inhibitors which, in their active forms, are single-polypeptide-chain proteins that exhibit serine protease inhibitor activity. These recombinant protease inhibitors are remarkably resistant to denaturation by heat and acids. Furthermore, these protease inhibitors retain their biological activity even after exposure to many proteolytic enzymes, such as chymotrypsin, mouse submaxillary protease and clostripain.

The coding strand of a DNA sequence which has been discovered to direct manufacture of these recombinant serine protease inhibitors is:

| 5' AGCGG | TAAAA | GCTTC | AAAGC | TGGCG | TATGC | CCGCC |
|---|---|---|---|---|---|---|
| GAAAA | AATCC | GCGCA | GTGTC | TGCGG | TACAA | AAAAC |
| CGGAA | TGCCA | GTCCG | ACTGG | CAGTG | CCCGG | GTAAA |
| AAACG | TTGTT | GCCCG | GACAC | CTGCG | GCATC | AAATG |
| CCTGG | ATCCG | GTTGA | TACCC | CGAAC | CCGAC | TCGTC |
| GAAAA | CCGGG | TAAAT | GCCCG | GTAAC | CTATG | GCCAG |
| TGTCT | GATGC | TGAAC | CCGCC | GAACT | TCTGC | GAAAT |
| GGACG | GCCAG | TGTAA | ACGAG | ATCTG | AAATG | CTGTA |
| TGGGT | ATGTG | CGGCA | AATCT | TGTGT | TTCCC | CGGTA |
| AAAGC | ATAA | | | | | 3' |

The nucleotides represented by the foregoing abbreviations are set forth in the Detailed Description of the Preferred Embodiment.

The coding strand for a second, preferred DNA sequence which has been discovered to direct manufacture of these recombinant serine protease inhibitors, particularly a secretory leukocyte protease inhibitor (SLPI) of the present invention, is:

```
5'  TCTGG TAAAA GCTTC AAAGC TGGCG TATGC CCGCC

GAAAA AATCC GCGCA GTGTC TGCGG TACAA AAAAC

CGGAA TGCCA GTCCG ACTGG CAGTG CCCGG GTAAA

AAACG TTGTT GCCCG GACAC CTGCG GCATC AAATG

CCTGG ATCCG GTTGA TACCC CGAAC CCGAC TCGTC

GAAAA CCGGG TAAAT GCCCG GTAAC CTATG GCCAG

TGTCT GATGC TGAAC CCGCC GAACT TCTGC GAAAT

GGACG GCCAG TGTAA ACGAG ATCTG AAATG CTGTA

TGGGT ATGTG CGGCA AATCT TGTGT TTCCC CGGTA

AAAGC ATAA                                 3'
```

To further achieve the objects and in accordance with the purposes of the present invention, a recombinant DNA method is disclosed which results in microbial manufacture of the instant serine protease inhibitors using either the natural DNA sequence isolated from a cDNA or genomic DNA library or synthetic DNA sequences such as those referred to above. This recombinant DNA method comprises:

(a) Preparation of a DNA sequence capable of directing a host microorganism to produce a protein having serine protease inhibitor activity, preferably leukocyte elastase inhibitor activity;

(b) Cloning the DNA sequence into a vector capable of being transferred into and replicating in a host microorganism, such vector containing operational elements for the DNA sequence;

(c) Transferring the vector containing the DNA sequence and operational elements into a host microorganism capable of expressing the protease inhibiting protein;

(d) Culturing the microorganism under conditions appropriate for amplification of the vector and expression of the inhibitor;

(e) Harvesting the inhibitor; and (f) Permitting the inhibitor to assume an active tertiary structure whereby it possesses serine protease inhibitor activity.

To facilitate identification and isolation of natural DNA sequences for use in the present invention, the present inventors have developed a human parotid tissue cDNA library. This library contains the genetic information capable of directing a cell to synthesize the serine protease inhibitors of the present invention. Other natural DNA sequences which may be used in the recombinant DNA methods set forth herein may be isolated from a human genomic library.

The synthetic DNA sequences useful in the processes of the present invention may be prepared by polynucleotide synthesis and sequencing techniques known to those of ordinary skill in the art. The natural DNA sequences useful in the foregoing process may be identified and isolated through a method comprising:

(a) Preparation of a human cDNA library from cells, preferably parotid cells, capable of generating a serine protease inhibitor;

(b) Screening the human DNA library with a probe which is capable of binding to the protease inhibitor gene or screening with an assay which is capable of detecting a protein produced by the protease inhibitor gene;

(c) Identification of at least one clone containing the gene coding for the inhibitor by virtue of the ability of the clone to bind at least one probe for the gene or to express its protein product;

(d) Isolation of the gene coding for the inhibitor from the clone(s) identified; and (e) Linking the gene, or suitable fragments thereof, to operational elements necessary to maintain and express the gene in a host microorganism.

The natural DNA sequences useful in the foregoing process may also be identified and isolated through a method comprising:

(a) Preparation of a human genomic DNA library, preferably propagated in a recArecBC *E. coli* host;

(b) Screening the human genomic DNA library with a probe which is capable of binding to a serine protein inhibitor gene or screening with an assay which is capable of detecting a protein produced by the protease inhibitor gene;

(c) Identification of at least one clone containing the gene coding for the inhibitor by virtue of the ability of the clone to bind at least one probe for the gene or to express its protein product;

(d) Isolation of the gene coding for the inhibitor from the clone or clones identified; and (e) Linking the gene, or suitable fragments thereof, to operational elements necessary to maintain and express the gene in a host microorganism.

Moreover, to achieve the objects and in accordance with the purposes of the present invention, pharmaceutically useful analogs of the serine protease inhibitor may be produced by the above-recited recombinant DNA method by altering the synthetic DNA sequence or the natural DNA segment, through recombinant DNA techniques, to create a gene capable of inducing expression of the desired analog when cloned into an appropriate vector and transferred into an appropriate host microorganism.

Additionally, to achieve the objects and in accordance with the purposes of the present invention, pharmaceutical compositions containing, as an active ingredient, a recombinant protease inhibitor in accordance with the present invention, or its biologically active analog produced by the above-recited recombinant DNA methods, are disclosed.

The accompanying drawings, which are incorporated herein and constitute a part of this application, illustrate various plasmids useful in this invention and, together with the description, serve to explain the principles of the invention.

DESCRIPTION OF THE PREFERRED EMBODIMENTS

Figure 1:
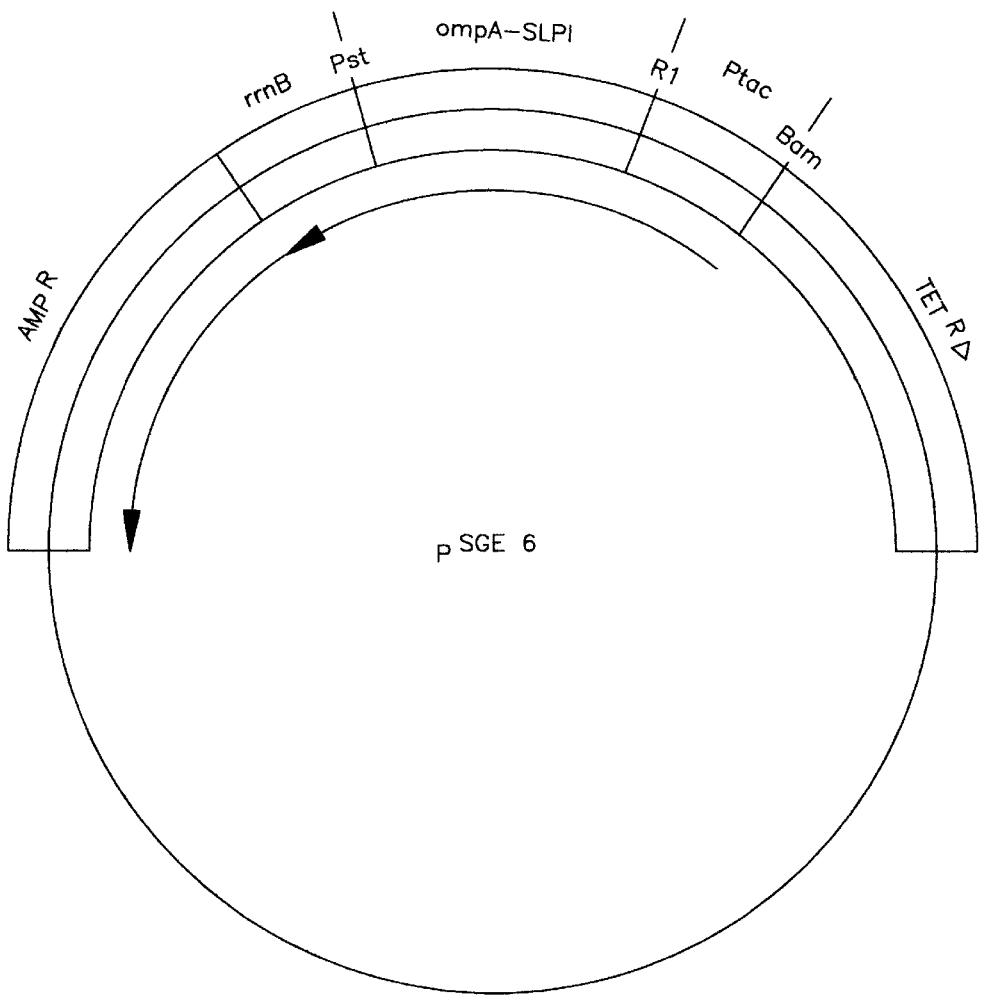
FIG. 1 is a map of plasmid pSGE6.

Reference will now be made in detail to the presently preferred embodiments of the invention, which, together with the following example, serve to explain the principles of the invention.

As noted above, the present invention relates to protease inhibitors which have been isolated in a purified form. Preferably, the serine protease inhibitors of the present invention are single-polypeptide-chain protein s which are substantially homologous to, and most preferably biologically equivalent to, native serine protease inhibitors isolated from human parotid secretions. By "biologically equivalent," as used throughout the specification and claims, it is meant that the compositions are capable of preventing protease induced tissue damage of the same type, but not necessarily to the same degree, as the native protease inhibitor. By "substantially homologous," as used throughout the ensuing specification and claims, is meant a degree of homology to the native parotid inhibitor in excess of that displayed by previously reported single-polypeptide-chain serine protease inhibitor proteins. Preferably, the degree of homology is in excess of 40%, most preferably in excess of 50%, with a particularly preferred group of proteins being in excess of 60% homologous with the native parotid inhibitor. The percentage homology as above described is calculated as the percentage of the components found in the smaller of the two sequences that may also be found in the larger of the two sequences, a component being understood as a sequence of four, contiguous amino acids.

Preferred protease inhibitors produced by the present recombinant methods are described in U.S. patent application Ser. No. 678,823 of Robert C. Thompson et al. entitled "Serine Protease Inhibitors and Methods for Isolation of Same," filed Dec. 6, 1984 and U.S. patent application Ser. No. 803,423 of Robert C. Thompson et. al. entitled "Serine Protease Inhibitors and Methods for Isolation of Same," filed Dec. 2, 1985 issued as U.S. Pat. No. 4,760,130 on Jul. 26, 1988. Such protease inhibitors are remarkably resistant to denaturation by heat and acids and resistant to loss of activity when exposed to many proteolytic enzymes, including chymotrypsin, mouse submaxillary protease and clostripain. These inhibitors also have the ability to form the necessary disulfide bonds and undergo appropriate non-covalent interactions to assume an active tertiary structure capable of expressing serine protease inhibitor activity in the absence of a biochemical stimulus or, if the disulfide bonds have been broken and the non-covalent interactions have been disrupted, to re-form such bonds and interactions to regain such active tertiary structure in the absence of biochemical stimulus.

A preferred native serine protease inhibitor isolated from parotid secretions having these characteristics has been sequenced. The sequence was determined to be as follows:

Ser — Gly — Lys — Ser — Phe — Lys — Ala — Gly — Val — Cys — Pro — Pro — Lys — Lys — Ser — Ala — Gln — Cys — Leu — Arg — Tyr — Lys — Lys — Pro — Glu — Cys — Gln — Ser — Asp — Trp — Gln — Cys — Pro — Gly — Lys — Lys — Arg — Cys — Cys — Pro — Asp — Thr — Cys — Gly — Ile — Lys — Cys — Leu — Asp — Pro — Val — Asp — Thr — Pro — Asn — Pro — Thr — Arg — Arg — Lys — Pro — Gly — Lys — Cys — Pro — Val — Thr — Tyr — Gly — Gln — Cys — Leu — Met — Leu — Asn — Pro — Pro — Asn — Phe — Cys — Gly — Met — Asp — Gly — Gln — Cys — Lys — Arg — Asp — Leu — Lys — Cys — Cys — Met — Gly — Met — Cys — Gly — Lys — Ser — Cys — Val — Ser — Pro — Val — Lys — Ala.

The foregoing abbreviations correspond to the amino acid residues in the polypeptide as follows:

| Amino acid | Abbreviation |
|---|---|
| Alanine | Ala |
| Valine | Val |
| Leucine | Leu |
| Isoleucine | Ile |
| Proline | Pro |
| Phenylalanine | Phe |
| Tryptophan | Trp |
| Methionine | Met |
| Glycine | Gly |
| Serine | Ser |
| Threonine | Thr |
| Cysteine | Cys |
| Tyrosine | Tyr |
| Asparagine | Asn |
| Glutamine | Gln |
| Aspartic acid | Asp |
| Glutamic acid | Glu |
| Lysine | Lys |
| Arginine | Arg |
| Histidine | His |

It has been found that these protease inhibitors manufactured by the recombinant DNA methods disclosed herein have more than one distinct domain. By more than one distinct domain it is meant that the protein has multiple active sites which are functional against different enzymes. The presence and location of these sites have been determined by the discovery of a substantial homology between at least two portions of the protease inhibitor. It is believed that the presence of distinct domains confers on the instant protease inhibitors the ability to inhibit a wide variety of serine proteases that includes both leukocyte elastase and trypsin.

It has further been noted that, due to the plurality of distinct domains of these protease inhibitors, the protease inhibitors may serve as frameworks on which various other active sites may be constructed to create protease inhibitors having additional properties. The preferred embodiment of the present invention involves production of a protease inhibitor that inhibits leukocyte elastase, cathepsin G, pancreatic elastase and trypsin. These enzymes are all members of a class of proteases known as serine proteases that share a common mechanism and many structural features. It is believed that, through manipulation of a few amino acid side-chains on the protease inhibitors produced by the present invention, a multiplicity of inhibitors may be created, each being capable of inhibiting at least one member of the whole class of serine proteases. Furthermore, such side-chain modifications can be expected to yield a plurality of inhibitors having improved inhibitory properties with respect to particular members of the class of serine proteases described above.

The amino acid-side chain changes required to attain these goals are suggested by certain elements of structural similarity between the preferred inhibitor produced by the present invention and other serine protease inhibitors for which the important functional part of the inhibitor has been elucidated through X-ray crystallography. Those elements of structural similarity incude amino acids 17 to 29 and amino acids 70 to 83 of the preferred serine protease inhibitor produced by the present invention described above. The changes suggested to improve the inhibitor's activity, either in terms of quantity or quality, toward trypsin-like serine proteases include changing one or more of amino acid 20 from Arg to Lys, amino acid 72 or 74 from Leu to Lys or Arg, and amino acid 73 from Met to Lys or Arg.

The changes suggested to improve the inhibitor's activity, either in terms of quantity or quality, toward chymotrypsin-like serine proteases, including cathepsin G, include changing one or more of amino acid 20 from Arg to Phe, Tyr or Trp, amino acid 72 or 74 from Leu to Phe, Tyr or Trp, and amino acid 73 from Met to Phe, Tyr, or Trp.

The changes suggested to improve the inhibitor's activity, either in terms of quantity or quality, toward pancreatic-elastase-like serine proteases include changing one or more of amino acid 20 from Arg to Ala, amino acid 72 or 74 from Leu to and amino acid 73 from Met to Ala.

It must be borne in mind in the practice of the present invention that the alteration of amino acid sequences to confer new protease inhibiting properties on the present proteins may disrupt the inhibitor's activity toward leukocyte elastase or toward trypsin. Such effects may be determined by routine experimentation following the teachings of the present invention.

Further, it is contemplated that substitution of discrete amino acids or of discrete sequences of amino acids, as set forth above, may enhance either the leukocyte elastase inhibitory properties or the trypsin inhibitory properties of the present protease inhibitors while sacrificing some activity of the unenhanced domain. Indeed, the activity of any domain within the inhibitor protein may be eliminated entirely by appropriate amino-acid substitutions, thereby creating inhibitor proteins which are specific for one or some subset of the enzymes against which the protein is normally active. For example, substitution of Gly for Arg in position 20 deactivates the trypsin inhibitory domain while substitution of Gly for Met in the 73 position or for Leu in the 72 or 74 position deactivates the leukocyte elastase inhibitory domain. The domains may also be separated into separate proteins, each of which retains the desired inhibitory functions. The present claims extend to other processes for producing such inhibitors by these means.

The present inventors have discovered a synthetic DNA sequence which is capable of directing intracellular production of the above-discussed protease inhibitors. This sequence has the following structure:

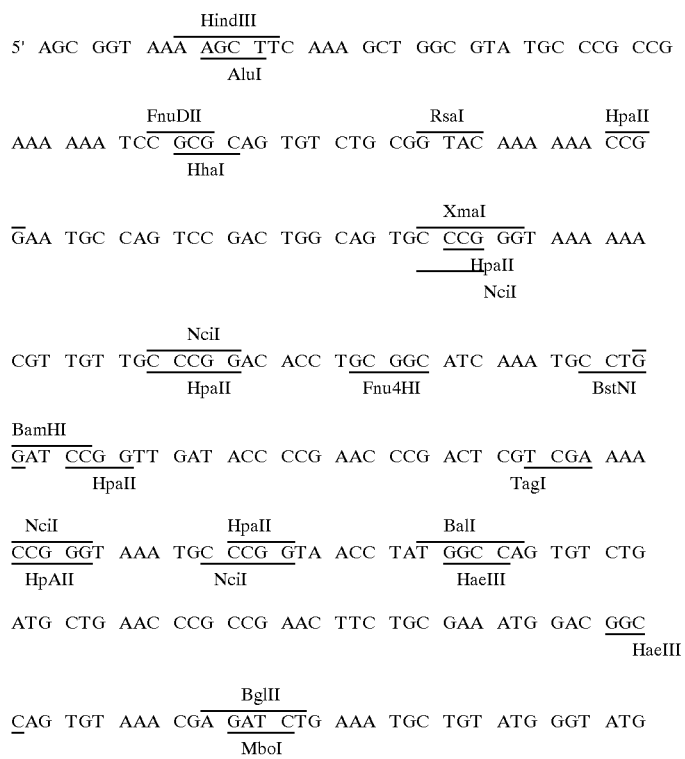

```
          Fnu4HI                              -continued
                                                    NciI
TGC  GGC  AAA  TCT  TGT  GTT  TCC  CCG  GTA  AAA  GCA  TAA
                                       HpaII
``` wherein the following nucleotides are represented by the abbreviations indicated below.

| Nucleotide | Abbreviation |
|---|---|
| deoxyadenylic acid | A |
| deoxyguanylic acid | G |
| deoxycytidylic acid | C |
| thymidylic acid | T |

The present inventors have discovered a second, preferred synthetic DNA sequence which is capable of directing extracellular production of the above-discussed protease inhibitors, particularly the secretory leukocyte protease inhibitor (SLPI) referred to above. This sequence has the following structure:

```
              HindIII
5'TCT  GGT  AAA  AGC TTC  AAA  GCT  GGC  GTA  TGC  CCG  CCG
                    AluI FnuDII            RsaI              HpaII
AAA  AAA  TCC  GCG CAG  TGT  CTG  CGG TAC  AAA  AAA  CCG
                HhaI XmaI
GAA  TGC  CAG  TCC  GAC  TGG  CAG  TGC  CCG GGT  AAA  AAA
                                     HpaII
                                     NciI HpaII
CGT  TGT  TGC  CCG GAC  ACC  TGC  GGC ATC  AAA  TGC  CTG
                NciI           Fnu4HI           BstNI BamHI
GAT  CCG  GTT  GAT  ACC  CCG  AAC  CCG  ACT  CGT CGA  AAA
     HpaII                                        TaqI HpaII       HpaII              BalI
CCG GGT  AAA  TGC CCG GTA  ACC  TAT  GGC   CAG  TGT  CTG
  NciI         NciI               HaeIII ATG  CTG  AAC  CCG  CCG  AAC  TTC  TGC  GAA  ATG  GAC  GGC
                                                        HaeIII BglII
CAG  TGT  AAA  CGA GAT CTG  AAA  TGC  TGT  ATG  GGT  ATG
                    MboI Fnu4HI                         NciI
TGC  GGC  AAA  TCT  TGT  GTT  TCC  CCG  GTA  AAA  GCA  TAA
                                   HpaII                  3'
```

Due to multiple domain structure of the instant protease inhibitors, as noted above, variations are contemplated in the synthetic DNA sequence set forth herein which will result in a DNA sequence which is capable of directing production of the serine protease inhibitor analogs as discussed above. In particular, preferred analogs of the serine protease inhibitors manufactured by recombinant DNA techniques according to the present invention have the amino acid sequence:

$R_1$ — Gly — Lys — Ser — Phe — Lys — Ala — Gly — Val — Cys — Pro — Pro — Lys — Lys — Ser — Ala — Gln — Cys — Leu — $R_2$ — Tyr — Lys — Lys — Pro — Glu — Cys — Gln — Ser — Asp — Trp — Gln — Cys — Pro — Gly — Lys — Lys — Arg — Cys — Cys — Pro — Asp — Thr — Cys — Gly — Ile — Lys — Cys — Leu — Asp — Pro — Val — Asp — Thr — Pro — Asn — Pro — Thr — Arg — Arg — Lys — Pro — Gly — Lys — Cys — Pro — Val — Thr — Tyr — Gly — Gln — Cys — $R_8$ — $R_3$ — $R_9$ — Asn — Pro — Pro — Asn — Phe — Cys — Glu — $R_4$ — Asp — Gly — Gln — Cys — Lys — Arg — Asp — Leu — Lys — Cys — Cys — $R_5$ — Gly — $R_6$ — Cys — Gly — Lys — Ser — Cys — Val — Ser — Pro — Val — Lys — $R_7$.

wherein, $R_1$ and $R_7$ are the same or different and are selected from the group consisting of a substituted or unsubstituted amino acid residue or derivative thereof; and $R_2$, $R_3$, $R_4$, $R_5$, $R_6$, $R_8$ and $R_9$ are the same or different and are selected from the group consisting of methionine, valine, alanine, phenylalanine, tyrosine, tryptophan, lysine, glycine and arginine.

It should be noted that the DNA sequence set forth above represents a preferred embodiment of the present invention. Due to the degeneracy of the genetic code, it is to be understood that numerous choices of nucleotides may be made which will lead to a DNA sequence capable of directing production of the instant protease inhibitors or their analogs. As such, DNA sequences which are functionally equivalent to the sequence set forth above or which are functionally equivalent to sequences which would direct production of analogs of the protease inhibitor produced pursuant to the amino acid sequence set forth above, are intended to be encompassed within the present invention. As an example of the codon substitutions that are contemplated as a result of the degenerate genetic code, the following diagram represents additional DNA sequences which are intended to be included within the scope of the present invention for manufacture of the preferred amino acid sequence enumerated above. By following the example for determining equivalent DNA sequences for production of this protein, those of ordinary skill in the art will be able to determine equivalent DNA sequences for production of analogs of the preferred amino acid sequence as well.

```
                                                    10
        Ser   Gly   Lys   Ser   Phe   Lys   Ala   Gly   Val   Cys   Pro   Pro   Lys   Lys   Ser   Ala
    5'  TCN   GGN   AAP   TCN   TTQ   AAP   GCN   GGN   GTN   TGQ   CCN   CCN   AAP   AAP   TCN   GCN
        AGQ               AGQ                                                               AGQ 20                                              30
        Gln   Cys   Leu   Arg   Tyr   Lys   Lys   Pro   Glu   Cys   Gln   Ser   Asp   Trp   Gln   Cys
        CAP   TGQ   CTN   CGN   TAQ   AAP   AAP   CCN   GAP   TGQ   CAP   TCN   GAQ   TGG   CAP   TGQ
                    TTP   AGP                                           AGQ
```

-continued

|  |  |  |  |  |  |  |  |  | 40 |  |  |  |  |  |  |
|---|---|---|---|---|---|---|---|---|---|---|---|---|---|---|---|
| Pro | Gly | Lys | Lys | Arg | Cys | Cys | Pro | Asp | Thr | Cys | Gly | Ile | Lys | Cys | Leu |
| CCN | GGN | AAP | AAP | CGN | TGQ | TGQ | CCN | GAQ | ACN | TGQ | GGN | ATQ | AAP | TGQ | CTN |
|  |  |  |  | AGP |  |  |  |  |  |  |  | ATA |  |  | TTP |

|  | 50 |  |  |  |  |  |  |  |  |  | 60 |  |  |  |  |
|---|---|---|---|---|---|---|---|---|---|---|---|---|---|---|---|
| Asp | Pro | Val | Asp | Thr | Pro | Asn | Pro | Thr | Arg | Arg | Lys | Pro | Gly | Lys | Cys |
| GAQ | CCN | GTN | GAQ | ACN | CCN | AAQ | CCN | ACN | CGN | CGN | AAP | CCN | GGN | AAP | TGQ |
|  |  |  |  |  |  |  |  |  | AGP | AGP |  |  |  |  |  |

|  |  |  |  |  | 70 |  |  |  |  |  |  |  |  |  | 80 |
|---|---|---|---|---|---|---|---|---|---|---|---|---|---|---|---|
| Pro | Val | Thr | Tyr | Gly | Gln | Cys | Leu | Met | Leu | Asn | Pro | Pro | Asn | Phe | Cys |
| CCN | GTN | ACN | TAQ | GGN | CAP | TGQ | CTN | ATG | CTN | AAQ | CCN | CCN | AAQ | TTQ | TGQ |
|  |  |  |  |  |  |  | TTP |  | TTP |  |  |  |  |  |  |

|  |  |  |  |  |  |  |  |  | 90 |  |  |  |  |  |  |
|---|---|---|---|---|---|---|---|---|---|---|---|---|---|---|---|
| Glu | Met | Asp | Gly | Gln | Cys | Lys | Arg | Asp | Leu | Lys | Cys | Cys | Met | Gly | Met |
| GAP | ATG | GAQ | GGN | CAP | TGQ | AAP | CGN | GAQ | CTN | AAP | TGQ | TGQ | ATG | GGN | ATG |
|  |  |  |  |  |  |  | AGP |  | TTP |  |  |  |  |  |  |

|  |  |  |  |  |  |  |  |  | 100 |  |
|---|---|---|---|---|---|---|---|---|---|---|
| Cys | Gly | Lys | Ser | Cys | Val | Ser | Pro | Val | Lys | Ala |
| TGQ | GGN | AAP | TCN | TGQ | GTN | TCN | CCN | GTN | AAP | GCN 3' |
|  |  |  | AGQ |  |  | AGQ |  |  |  |  |

In the above sequence, abbreviations used are intended to represent the nucleotides indicated below.

| Nucleotide | Abbreviation |
|---|---|
| A, G, C, T | N |
| A, G | P |
| C, T | Q |

When selecting codons for use in the synthetic DNA sequences of the present invention, including that set forth immediately above, it is preferred that the codons used to indicate a particular amino acid be those which are associated with highly expressed proteins. Examples of these preferred codons are set forth in part in Grantham, R. et al., "Codon Catalog Usage Is a Genome Strategy Modulated For Gene Expressivity" in Nucleic Acids Research 9:r43 (1981). The preferred DNA sequence of the present invention was chosen by selecting *Escherichia coli* sequence codons for any of the degenerate sequences.

Additionally, it is desired to select codons which facilitate the alteration of the synthetic DNA sequence to construct additional synthetic DNA sequences which are capable of directing production of analogs of the present protease inhibitors. In particular, it is preferred that nucleotide sequences are selected which, if possible, create restriction endonuclease sites at, or close to, positions in the synthetic DNA sequence into which it may be desired to insert additional codons or at which sites it may be desired to replace a codon so that analogs may be created. In the preferred embodiment of the DNA sequence of the present invention, the restriction sites are indicated below the nucleotide sequence set forth above.

Methods of creating the synthetic DNA sequences contemplated herein are generally within the ambit of routine tasks performed by one of ordinary skill in the art guided by instant disclosure. An example of a suitable method which may be used to obtain the synthetic DNA sequence disclosed herein is set forth in Matteacci, M. D. and Caruthers, M. H., J.Am.Chem.Soc. 103:3185 (1981) and Beaucage, S. L. and Caruthers, M. H., Tetrahedron Lett. 22:1859 (1981), both of which are specifically incorporated herein by reference.

In an alternate embodiment of the present invention, a DNA sequence has been isolated from a human genomic library which encodes a preferred secretory leukocyte protease inhibitor (SLPI) of the present invention. This sequence, encoding from the fourth codon and including the introns as presently known to the inventors, is as follows:

```
        EcoR1               20                  40                  60
        GAATTCTGGTGGGGCCACACCCACTGGTGAAAGAATAAATAGTGAGGTTTGGATTGGCC
        ---------INTRON-----------------------------------------------

80                  100                 120
        ATCAGAGTCACTCCTGCCTTCACCATGAAGTCCAGCGGCCTCTTCCCCTTCCTGGTGCTG
        --------------------------------------------------------------

140                 160                 180
        CTTGCCCTGGAACTCTGGCACTTGGGCTTGGAAGGCTCTGAAATGTAAGTTGGAGTCACT
        --------------------------------------------------------------

Pst1                220                 240
        CTGTCTAATCTGGGCTGCAGGGTCAGAGGTGGGGTCTCCTTGTGGTGTGGGTGTGTCCCC
        --------------------------------------------------------------

260                 280                 300
        GTCTGTAGGCTCTGATCCCTCAGCTTAGTTTCGGGAGACCTCCCTGAGGGTGGAATACAT
        --------------------------------------------------------------
```

```
                      SacI         320                          340                          360
                GTCTGGCTGAGCTCCAAGGTTTGTGTGACAGTTTGAGCTTCTGGAAATGCTTCCTCTATG
                -----------------------------------------------------------

380                          400                          420
                CAGCCATGCTGTCAGCCCAGGTCCCACTCTCTCTCTCTCTCTCTCTCTCTCTCTCTCTCA
                -----------------------------------------------------------

440                          460                          480
                TACTCCGCCTTCTTCTTCACCTTGCTGCGACTCTCAAATCATTAGTTTCTGACTCTGCTT
                -----------------------------------------------------------

500                          520                          540
                CCGTTGTGTCTTTGCTTCTGCTATTTTGTCTCTGTGCTTCTCGCTTGGGATTTAGCTCTC
                -----------------------------------------------------------

560                          580                          600
                AACTTCTCTCACACTGGTTCTATTTATCTTTGTTTACCTCTCTCCATCTCCATCACTCCC
                -----------------------------------------------------------

620                          640                          660
                AGCCTTCCTCTCTGCCTTTGTGTAGCCTTGTTTTGCTCTTGGGTGGAGGTCTTGACTAGA
                -----------------------------------------------------------

680                          700                          720
                AGCCTGCTGCCCTTTTCTTGGGTGTGAAACGTCCCCTGTCCATTTGTCTAATTTAATCAA
                -----------------------------------------------------------

740                          760                          780
                GCCCATCAATACACCTGGAGATCAGGCAGGCATGACCTTTGGGCTTTGTGGACAGCTACT
                -----------------------------------------------------------

800                          820                          840
                GAGGTAAGGGTCTCTCCCCCTCAAAAGTGGTGCTTTGTTCAGGAGGCATGATGGGTCCTC
                -----------------------------------------------------------

860                          880                          900
                AGTACCCAGCCTCCTCCTACCTCTTGACTTTCTCTTCAAAAGCCTTCAAAGCTGGAGTCT
                --------------END  OF  INTRON----------------    F    K    A    G    V 920                          940                          960
                GTCCTCCTAAGAAATCTGCCCAGTGCCTTAGATACAAGAAACCTGAGTGCCAGAGTGACT
                  C    P    P    K    K    S    A    Q    C    L    R    Y    K    K    P    E    C    Q    S    D 980                         1000                         BamHI
                GGCAGTGTCCAGGGAAGAAGAGATGTTGTCCTGACACTTGTGGCATCAAATGCCTGGATC
                  W    Q    C    P    G    K    K    R    C    C    P    D    T    C    G    I    K    C    L    D 1040                         1060                         1080
                CTGTTGACACCCCAAACCCAAGTAAGCAGGTCGGGGAACTGGGTAGAGAGATAGCCTGGG
                  P    V    D    T    P    N    P       -----START  INTRON---------------------

1100                         1120     StuI                1140
                GACACAGCATTAGAGGGACGGAACTGGGTGATGGGTCCTGCCAGGCCTCCTTGTCAATGC
                -----------------------------------------------------------

1160              PvuII                                   1200
                CGTAGTGAGTCACAGTGCCCTAAGAGAAGTAGCCAGCTGGTGAAGCAGCGGGCATTTAGA
                -----------------------------------------------------------

1220                         1240                         1260
                TAGCCAGGTAGTTGGAAGCCTCCCACCTAGTCAGCACTGGGCGGCTGGCACCTGCATAAT
                _____

1280                         1300                         1320
                GGGGGGCCTGAAGTTCTAGGAGAGCCAGGTGCTATGTTTGGGGGCCGCCTTAGGGAGAAG
                _____

1340                         1360                         1380
                GTGGTGGTGATAGAGGTGGGGAGGGGATGATCCCCCCTGCTGAAGCTGGACGAGGGGCTC
                -----------------------------------------------------------

1400                         1420     StuI                1440
                ACTCTAAAAAGTGGGGATGGGAGGGGTTGTATAAAGTACAAGGCCTCTGACCGGTAGCCT
                ---------------------------------------------END  OF  INTRON------

1460                         1480                         1500
                CACTCTCACCCAACCCAGCAAGGAGGAAGCCTGGGAAGTGCCCAGTGACTTATGGCCAAT
                ------------------    R    R    K    P    G    K    C    P    V    T    Y    G    Q 1520                         1540                         1560
                GTTTGATGCTTAACCCCCCCAATTTCTGTGAGATGGACCAGTGCAAGCGTGACTTGA
                  C    L    M    L    N    P    P    N    F    C    E    M    D    G    Q    C    K    R    D    L
```

-continued

```
                     1580                    1600                    1620
AGTGTTGCATGGGCATGTGTGGGAAATCCTGCGTTTCCCCTGTGAAAGGTAAGCAGGGGA
 K  C  C  M  G  M  C  G  K  S  C  V  S  P  V  K  --START INTRON

SacI      1640                    1660                    1680
CGAGGGCACACTGAGCTCCCTCAGCCCTCTCAGCCTCAACCCTCTGGAGGCCCAGGCATA
------------------------------------------------------------

1700                    1720                    1740
TGGGCAGGGGGACTCCTGAACCCTACTCCAAGCACAGCCTCTGTCTGACTCCCTTGTCCT
------------------------------------------------------------

1760                    1780                    1800
TCAAGAGAACTGTTCTCCAGGTCTCAGGGCCAGGATTTCCATAGGAGTCGCCTGTGGCTT
------------------------------------------------------------

1820                    1840                    1860
TGATTCTATTCTAGTGTCTCTGGGTGGGGGTCCTGGGCAAGTGTCTTTCTGAGTCTAGTT
------------------------------------------------------------

1880                    1900                    1920
TCTTTATCGGTAAAATGTACATAATGAGATGAAAGTGCTCTGCAAAGACCTATGTGCACT
------------------------------------------------------------

1940                    1960                    1980
AAGAATTATTATTCAGGTGTTTCCATCATGTTTTCTGAGGTGAAATCACAAAGGATCAGT
------------------------------------------------------------

2000                    2020                    2040
GGAGTTTGAGGATTATCTAGTTCAATGCTTTGAGTTTAGAGTTTTACGTGAAAATGAGAC
------------------------------------------------------------

2060                    2080                    2100
TTGTCTCCTGACACTAAGTCTCTCTCAACTATAGCGCTATCTTGCTATTTTCTCTATCTC
------------------------------------------------------------

2120                    2140                    2160
AGAAGGATCCTTGGGCAGGAGGAAGGATGTGGATATATGATTTGGCTGGTTTCTATGCTG
------------------------------------------------------------

2180                    2200                    2220
AAGCTCTGATCTGATTTTCTCTCACAGCTTGATTCCTGCCATATCGGAGGAGGCTCTGGA
-PROBABLE-----------------      STOP
 END OF INTRON 2240                    2260
GCCTGCTCTGTGTGGTCCAGGTCCTTTCCACCCTGAGCTTGGCTCCACCACTGGT
```

In this sequence, the abbreviations used for the amino acid residues are the one-letter abbreviations which are commonly employed and may be found, for example, in Biochemistry by A. L. Lehninger, 2nd ed., Worth Publishers, Inc., New York, N.Y. (1976), pg. 72.

Using this sequence and the amino acid sequence data contained herein, a synthetic DNA sequence can be constructed, that, when added to the genomic sequence above, leads to a gene which codes for the entire protease inhibitor. Alternatively, probes may be constructed using the DNA sequence set forth above and used to retrieve a DNA segment from a human genomic library which has codons for the first three amino acids.

Additionally, such probes may be used to identify a human genomic sequence which contains an appropriate leader sequence. It is contemplated that this leader sequence, or any other appropriate leader sequence, could be used in conjunction with this genomic DNA sequence in a mammalian expression system.

In another alternate embodiment of the present invention, a cDNA clone has been isolated from a parotid library which encodes a DNA sequence capable of directing intracellular production of a preferred secretory leukocyte protease inhibitor of the present invention.

A recombinant DNA method for the manufacture of a protease inhibitor composed of a single polypeptide chain with at least one active site possessing serine protease inhibitor activity has been disclosed. In one embodiment of the invention, the active site functions in a manner biologically equivalent to that of the native leukocyte elastase inhibitor isolated from human parotid secretions. A natural or synthetic DNA sequence may be used to direct production of the protease inhibitors. This method comprises:

(a) Preparation of a DNA sequence capable of directing a host microorganism to produce a protein having serine protease inhibitor activity;

(b) Cloning the DNA sequence into a vector capable of being transferred into and replicated in a host microorganism, such vector containing operational elements for the DNA sequence;

(c) Transferring the vector containing the synthetic DNA sequence and operational elements into a host microorganism capable of expressing the protease inhibitor;

(d) Culturing the microorganism under conditions appropriate for amplification of the vector and expression of the inhibitor;

(e) Harvesting the inhibitor; and (f) Permitting the inhibitor to assume an active tertiary structure whereby it possesses serine protease inhibitory activity.

Synthetic DNA sequences contemplated for use in this method have been discussed in detail above. It is further contemplated, in an alternative embodiment, that natural DNA sequences may also be used in this method. These sequences include cDNA or genomic DNA segments. In a preferred version of this embodiment, it is contemplated that the natural DNA sequence will be obtained by a method comprising:

(a) Preparation of a human cDNA library from cells, preferably parotid cells, capable of generating a serine protease inhibitor;

(b) Probing the human DNA library with at least one probe capable of binding to the protease inhibitor gene or its protein product;

(c) Identification of at least one clone containing the gene coding for the inhibitor by virtue of the ability of the clone to bind at least one probe for the gene or its protein product;

(d) Isolation of the gene coding for the inhibitor from the clone or clones chosen;

(e) Linking the gene, or suitable fragments thereof, to operational elements necessary to maintain and express the gene in host microorganism.

The natural DNA sequences useful in the foregoing process may also be identified and isolated through a method comprising:

(a) Preparation of a human genomic DNA library, preferably propagated in a recArecBC *E. coli* host;

(b) Probing the human genomic DNA library with at least one probe capable of binding to a serine protein inhibitor gene or its protein product;

(c) Identification of at least one clone containing the gene coding for the inhibitor by virtue of the ability of the clone to bind at least one probe for the gene or its protein product;

(d) Isolation of the gene coding for the inhibitor from the clone(s) identified; and (e) Linking the gene, or suitable fragments thereof, to operational elements necessary to maintain and express the gene in a host microorganism.

In isolating a natural DNA sequence suitable for use in the above-method, it is preferred to identify the two restriction sites located within and closest to the end portions of the appropriate gene or sections of the gene. The DNA segment containing the appropriate gene is then removed from the remainder of the genomic material using appropriate restriction endonucleases. After excision, the 3' and 5' ends of the DNA sequence are reconstructed to provide appropriate DNA sequences capable of coding for the N- and C- termini of the serine protease inhibitor protein and capable of fusing the DNA sequence to its operational elements.

The vectors contemplated for use in the present invention include any vectors into which a DNA sequence as discussed above can be inserted, along with any preferred or required operational elements, and which vector can then be subsequently transferred into a host microorganism and replicated in such microorganism. Preferred vectors are those whose restriction sites have been well documented and which contain the operational elements preferred or required for transcription of the DNA sequence.

The "operational elements," as discussed herein, include at least one promoter, at least one operator, at least one leader sequence, at least one Shine-Dalgarno sequence, at least one terminator codon, and any other DNA sequences necessary or preferred for appropriate transcription and subsequent translation of the vector DNA. In particular, it is contemplated that such vectors will contain at least one origin of replication recognized by the host microorganism along with at least one selectable marker and at least one promoter sequence capable of initiating transcription of the synthetic DNA sequence. It is additionally preferred that the vector, in one embodiment, contains certain DNA sequences capable of functioning as regulators, and other DNA sequences capable of coding for regulator protein. These regulators, in one embodiment, serve to prevent expression of the synthetic DNA sequence in the presence of certain environmental conditions and, in the presence of other environmental conditions, allow transcription and subsequent expression of the protein coded for by the synthetic DNA sequence. In particular, it is preferred that regulatory segments be inserted into the vector such that expression of the synthetic DNA will not occur in the absence of, for example, isopropylthio-β-d-galactoside. In this situation, the transformed microorganisms containing the synthetic DNA may be grown to a desired density prior to initiation of the expression of the protease inhibitor. In this embodiment, expression of the desired protease inhibitor is induced by addition of a substance to the microbial environment capable of causing expression of the DNA sequence after the desired density has been achieved.

Additionally, it is preferred that an appropriate secretory leader sequence be present, either in the vector or at the 5' end of the synthetic DNA sequence. The leader sequence is in a position which allows the leader sequence to be immediately adjacent to the initial portion of the nucleotide sequence capable of directing expression of the protease inhibitor without any intervening translation termination signals. The presence of the leader sequence is desired in part for one or more of the following reasons: 1) the presence of the leader sequence may facilitate host processing of the initial product to the mature recombinant protease inhibitor; 2) the presence of the leader sequence may facilitate purification of the recombinant protease inhibitors, through directing the protease inhibitor out of the cell cytoplasm; 3) the presence of the leader sequence may affect the ability of the recombinant protease inhibitor to fold to its active structure through directing the protease inhibitor out of the cell cytoplasm.

In particular, the leader sequence may direct cleavage of the initial translation product by a leader peptidase to remove the leader sequence and leave a polypeptide with the prefered amino acid sequence which has the potential of serine protease inhibitory activity. In some species of host microorganisms, the presence of the appropriate leader sequence will allow transport of the completed protein into the periplasmic space, as in the case of *E. coli*. In the case of certain yeasts and strains of Bacilli and Pseudomonas, the appropriate leader sequence will allow transport of the protein through the cell membrane and into the extracellular medium. In this situation, the protein may be purified from extracellular protein.

Thirdly, in the case of some of the protease inhibitors prepared by the present invention, the presence of the leader sequence may be necessary to locate the completed protein in an environment where it may fold to assume its active structure, which structure possesses the appropriate elastase-inhibitor activity.

Additional operational elements include, but are not limited to, ribosome binding sites and other DNA sequences necessary for microbial expression of foreign proteins. In a preferred embodiment of the present invention, the sequence GAGGCGCAAAAA(ATG) would be used as the ribosome binding site. The operational elements as discussed herein are routinely selected by those of ordinary skill in the art in light of prior literature and the teachings contained herein. General examples of these operational elements are set forth in B. Lewin, *Genes,* Wiley & Sons, New York (1983), which is specifically incorporated herein by reference. The vectors as contemplated herein may be constructed in part from portions of plasmids pBR322 and/or pIQ.

In one preferred embodiment of the present invention, an additional DNA sequence is located immediately preceding the synthetic DNA sequence which codes for the protease inhibitor. The additional DNA sequence is capable of functioning as a translational coupler, i.e., it is a DNA sequence that encodes an RNA which serves to position ribosomes immediately adjacent to the ribosome binding site of the protease inhibitor RNA with which it is contiguous. In one embodiment of the present invention, the translational coupler may be derived using the DNA sequence TAACGAG-GCGCAAAAAATGAAAAAGACAGC-TATCGCGATCGGAGTGTAAGAAATG and methods currently known to those of ordinary skill in the art related to translational couplers. A second, preferred translational coupler has the DNA sequence TAACGAGGCG-CAAAAAATGAAAAAGACAGCTATCGC-GATCAAGGAGAAATAAATG.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth in Schoner et al., Proceedings of the National Academy of Sciences U.S.A., 81:5403–5407 (1984), which is specifically incorporated herein by reference.

In construction of the cloning vector of the present invention it should additionally be noted that multiple copies of the synthetic DNA sequence and its attendant operational elements may be inserted into each vector. In such an embodiment the host organism would produce greater amounts per vector of the desired protease inhibitor. The number of multiple copies of the DNA sequence which may be inserted into the vector is limited only by the ability of the resultant vector, due to its size, to be transferred into and replicated and transcribed in an appropriate host microorganism.

Additionally, it is preferred that the vector contain a selectable marker, such as a drug resistance marker or other marker which causes expression of a selectable trait by the host microorganism. In a particularly preferred embodiment of the present invention, the gene for tetracycline resistance is preferably included on the cloning vector.

Such a drug resistance or other selectable marker is intended in part to facilitate in the selection of transformants. Additionally, the presence of such a selectable marker on the cloning vector may be of use in keeping contaminating microorganisms from multiplying in the culture medium. In this embodiment, such a pure culture of the transformed host microorganisms would be obtained by culturing the microorganisms under conditions which require the induced phenotype for survival.

The vector thus obtained is then transferred into the appropriate host microorganism. It is believed that any micororganism having the ability to take up exogenous DNA and express those genes and attendant operational elements may be chosen. It is preferred that the host microorganism be a facultative anaerobe or an aerobe. Particular hosts which may be preferable for use in this method include yeasts and bacteria. Specific yeasts include those of the genus Saccharomyces, and especially *Saccharomyces cerevisiae.* Specific bacteria include those of the genera Bacillus, Escherichia, and Pseudomonas, especially *Bacillus subtilis* and *Escherichia coli.*

After a host organism has been chosen, the vector is transferred into the host organism using methods generally known by those of ordinary skill in the art. Examples of such methods may be found in Advanced Bacterial Genetics by R. W. Davis et al., Cold Spring Harbor Press, Cold Spring Harbor, New York, (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the synthetic genes.

If it is contemplated that the recombinant serine protease inhibitors will ultimately be expressed in yeast, it is preferred that the cloning vector first be transferred into *Escherichia coli,* where the vector would be allowed to replicate and from which the vector would be obtained and purified after amplification. The vector would then be transferred into the yeast for ultimate expression of the serine protease inhibitor.

The host microorganisms are cultured under conditions appropriate for the expression of the serine protease inhibitor. These conditions are generally specific for the host organism, and are readily determined by one of ordinary skill in the art, in light of the published literature regarding the growth conditions for such organisms, for example Bergey's Manual of Determinative Bacteriology, 8th Ed., Williams & Wilkins Company, Baltimore, Md., which is specifically incorporated herein by reference.

Any conditions necessary for the regulation of the expression of the DNA sequence, dependent upon any operational elements inserted into or present in the vector, would be in effect at the transformation and culturing stages. In one embodiment, the cells are grown to a high density in the presence of appropriate regulatory conditions which inhibit the expression of the DNA sequence. When optimal cell density is approached, the environmental conditions are altered to those appropriate for expression of the synthetic DNA sequence. It is thus contemplated that the production of the protease inhibitor will occur in a time span subsequent to the growth of the host cells to near optimal density, and that the resultant protease inhibitor will be harvested at some time after the regulatory conditions necessary for its expression were induced.

In a preferred embodiment of the present invention, the recombinant protease inhibitor is purified subsequent to harvesting and prior to assumption of its active structure. This embodiment is preferred as the inventors believe that recovery of a high yield of re-folded protein is facilitated if the protein is first purified. However, in one preferred, alternate embodiment, the protease inhibitor may be allowed re-fold to assume its active structure prior to purification. In yet another preferred, alternate embodiment, the protease inhibitor is present in its re-folded, active state upon recovery from the culturing medium.

In certain circumstances, the protease inhibitor will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. If the protease inhibitor does not assume its proper, active structure, any disulfide bonds which have formed and/or any noncovalent interactions which have occurred will first be disrupted by denaturing and reducing agents, for example, guanidinium chloride and β-mercaptoethanol, before the protease inhibitor is allowed to assume its active structure following dilution and oxidation of these agents under controlled conditions.

To regulate the expression of the protein in a form suitable for export to the periplasm of *E. coli*, the following regulatory elements were proposed: a tac promoter for initiation of transcription at high levels; a lac operator for transcription regulation; a lac repressor (lac I$^q$), to be coded elsewhere on the plasmid; an OmpA Shine-Dalgarno sequence to initiate translation at a high level; an OmpA leader to facilitate periplasmic export of the product; an Ala of an Ala-Ser junction between the protein sequence encoded by these operator elements and that encoded by the structural genes described above to dictate cleavage of the initial product to yield the mature leukocyte elastase inhibitor. All of these features are incorporated into the following DNA sequence:

| CTGCA | GCTGT | TGACA | ATTAA | TCATC | GGCTC | GTCTC | GTATA | ATGTG | ATAAC | GAGGC |
|-------|-------|-------|-------|-------|-------|-------|-------|-------|-------|-------|
| GCAAA | AAATG | AAAAA | GACAG | CTATC | GCGAT | CGCAG | TGGCA | | | |
| CTGGC | TGGTT | TCGCT | ACCGT | AGCGC | AGGCC. | | | | | |

It is to be understood that application of the teachings of the present invention to a specific problem or environment will be within the capabilities of one having ordinary skill in the art in light of the teachings contained herein. Examples of the products of the present invention and representative processes for their isolation and manufacture appear in the following example.

EXAMPLE 1

On the basis of the amino acid sequence described above, the codon usage in highly expressed genes of *Escherichia coli*, and the provision of convenient restriction endonuclease cleavage sites, the following DNA sequence was proposed:

To regulate the expression of the protein in a form such that the protein remains in the *E. coli* cytoplasm, the following operational elements are proposed: the tac promoter; the lac operator, and the lac repressor (lac I$^q$); a consensus of Shine-Dalgarno sequences; and, to initiate a high level of translation, a fragment of the OmpA leader peptide to be used as a translational coupler. The translational coupling sequence comprises the DNA coding for the translation initiation region of the OmpA gene, the first eight amino acids of the OmpA leader peptide, the consensus Shine-Dalgarno sequence described above and a translational terminator. The translational coupling sequence is to be inserted between the promoter and the translation initiation site of the serine protease inhibitor gene, overlapping the latter. All of these features are incorporated into the following DNA sequence:

```
                  HindIII
  5'AGC GGT AAA AGC TTC AAA GCT GGC GTA TGC CCG CCG
                  AluI FnuDII              RsaI          HpaII
  AAA AAA TCC GCG CAG TGT CTG CGG TAC AAA AAA CCG
                  HhaI XmaI
  GAA TGC CAG TCC GAC TGG CAG TGC CCG GGT AAA AAA
                                          HpaII NciI NciI
  CGT TGT TGC CCG GAC ACC TGC GGC ATC AAA TGC CTG
            HpaII         Fnu4HI                  BstNI BamHI
  GAT CCG GTT GAT ACC CCG AAC CCG ACT CGT CGA AAA
      HpaII                              TagI NciI            HpaII           BalI
  CCG GGT AAA TGC CCG GTA ACC TAT GGC CAG TGT CTG
  HpaII          NciI               HaeIII ATG CTG AAC CCG CCG AAC TTC TGC GAA ATG GAC GGC
                                              HaeIII BglII
  CAG TGT AAA CGA GAT CTG AAA TGC TGT ATG GGT ATG
                  MboI Fnu4HI                  NciI
  TGC GGC AAA TCT TGT GTT TCC CCG GTA AAA GCA TAA 3'
                            HpaII
```

| | | | | | | | | | | |
|---|---|---|---|---|---|---|---|---|---|---|
| CTGCA | GCTGT | TGACA | ATTAA | TCATC | GGCTC | GTCTC | GTATA | ATGTG | ATAAC | GAGGC |
| GCAAA | AAATG | AAAAA | GACAG | CTATC | GCGAT | CGCAG | TGTAA | GAAAT | G. | |

A. Construction of Gene Fragments

To construct the above sequences, the following deoxyribonucleotides are synthesized using the ABI DNA synthesizer (Foster City, Calif.). The products are purified by polyacrylamide gel electrophoresis as described in the ABI instrument manual. They are 5' phosphorylated using T4 polynucleotide kinase and ATP using standard means.

The following group of oligonucleotide sequences are used to construct fragment Aa.

Oligonucleotide Aa1 is:
GCTGT TGACA ATTAA TCAT.
Oligonucleotide Aa2 is:
CGGCT CGTAT AATGT GTGGA ATTGT GAGCG GATAA CAATT T.
Oligonucleotide Aa3 is:
CACAC ATAAC GAGGC GCAAA AA.
Oligonucleotide Aa4 is:
ATGAA AAAGA CAGCT ATCGC GATCG.
Oligonucleotide Aa5 is:
CAGTG GCACT GGCTG GTTTC GCTAC CGTAG CGCAG GCCAG CGGTA AA.
Oligonucleotide Aa6 is:
GAGCC GATGA TTAAT TGTCA ACAGC TGCA.
Oligonucleotide Aa7 is:
TCCGC TCACA ATTCC ACACA TTATA C.
Oligonucleotide Aa8 is:
CCTCG TTATG TGTGA AATTG TTA.
Oligonucleotide Aa9 is:
GCCAC TGCGA TCGCG ATAGC TGTCT TTTTC ATTTT TTGCG.
Oligonucleotide Aa10 is:
AGCTT TTACC GCTGG CCTGC GCTAC GGTAG CGAAA CCAGC CAGT.

The following oligonucleotide sequences are assembled to make up fragment Ab.
Nucleotide Ab1 is:
GCTGT TGACA ATTAA TCAT.
Nucleotide Ab2 is:
CGGCT CGTAT AATGT GTGGA ATTGT GAGCG GATAA CAATT T.
Nucleotide Ab3 is:
CACAC ATAAC GAGGC GCAAA AA.
Nucleotide Ab4 is:
ATGAA AAAGA CAGCT ATCGC GATCG.
Nucleotide Ab5 is:
GAGTG TAAGA AATGA GCGGT AAA.
Nucleotide Ab6 is:
GAGCC GATGA TTAAT TGTCA ACAGC TGCA.
Nucleotide Ab7 is:
TCCGC TCACA ATTCC ACACA TTATA C.
Nucleotide Ab8 is:
CCTCG TTATG TGTGA AATTG TTA.
Nucleotide Ab9 is:
AGCTT TTACC GCTCA TTTCT TACAC TCCGA TCGCG ATAGC TGTCT TTTTC ATTTT TTGCG.

The following are the oligonucleotide sequences assembled to construct fragment B.
Oligonucleotide B1 is:
AGCTT CAAAG CTGGC GTATG CCCGC CGAAA AAATC CGCG.
Oligonucleotide B2 is:
CAGTG TCTGC GGTAC AAAAA ACCGG AATGC CAG.
Oligonucleotide B3 is:
TCCGA CTGGC AGTGC CCGGG TAAAA AACGT TGTTG C.
Oligonucleotide B4 is:
CCGGA CACCT GCGGC ATCAA ATGCC TG.
Oligonucleotide B5 is:
GATCC AGGCA TTTGA TGCCG CAGGT GTCCG GGCAA CAACG TTTTT TACCC GGGCA.
Oligonucleotide B6 is:
CTGCC AGTCG GACTG GCATT CCGGT TTTTT GTACC G.
Oligonucleotide B7 is:
CAGAC ACTGC GCGGA TTTTT TCGGC GGGCA TACGC CAGCT TGA.

The following are the oligonucleotide sequences used to construct fragment C.
Oligonucleotide C1 is:
GATCC GGTTG ATACC CCGAA CCCG.
Oligonucleotide C2 is:
ACTCG TCGAA AA.
Oligonucleotide C3 is:
CCGGG TAAAT GCCCG GTAAC CTATG GC.
Oligonucleotide C4 is:
CAGTG TCTGA TGCTG AACCC GCCGA AC.
Oligonucleotide C5 is:
TTCTG CGAAA TGGAC GGCCA GTGTA AACGA GAT.
Oligonucleotide C6 is:
CTAGA TCTCG TTTAC ACTGG CCGTC CATTT CGCAG AAGTT.
Oligonucleotide C7 is:
CGGCG GGTTC AGCAT CAGAC ACTGG CCATA GGTTA CCGGG CA.
Oligonucleotide C8 is:
TTTAC CCGGT TTTCG ACGAG TCGGG TT.
Oligonucleotide C9 is:
CGGGG TATCA ACCG.

The following group of oligonucleotide sequences are assembled to form fragment D.
Oligonucleotide D1 is:
GATCT GAAAT GCTGT ATGGG TATGT GCGGC.
Oligonucleotide D2 is:
AAATC TTGTG TTTCC CCGGT AAAAG CATAA G.
Oligonucleotide D3 is:
TCGAC TTATG CTTTT ACCGG GGAAA CACAA GATTT GCCGC A.
Oligonucleotide D4 is:
CATAC CCATA CAGCA TTTCA.

The following groups of oligonucleotides are mixed and annealed under standard conditions and ligated to each other and to cloning and sequencing vectors M13 mp18 and 19 cut with appropriate restriction endonucleases using T4 DNA ligase under standard conditions. The products are used to transform E. coli JM105 and clones containing the DNA of interest are selected from white plaques in IPTG- Xgal plates, and further screened by hybridization with $^{32}$P labelled oligonucleotides selected from the group used in the annealing step. The insert structure is confirmed by dideoxy sequencing of the cloned DNA using a universal primer.

Group Aa contains oligonucleotides Aa1–Aa10 which are ligated to M13 mp18 and 19 cut with PstI and HindIII. Group Ab contains oligonucleotides Ab1–Ab9, which are ligated to M13 mp18 and 19 cut with PstI and HindIII. Group B, which contains oligonucleotides B1 to B7, is ligated to M13 mp18 and 19 cut with HindIII and BamHI. Group C, which contains oligonucleotides C1 to C9, is ligated to M13 mp18 and 19 cut with BamHI and XbaI. Group D, which contains oligonucleotides D1 to D4, is ligated to M13 mp18 and 19 cut with BamHI and SalI.

M13 replicative form DNA is recovered from the clone having the desired insert DNA by standard means. The insert DNA corresponding to Group Aa is excised from the M13 DNA by cutting the DNA with appropriate restriction endonucleases and is purified by polyacrylamide gel electrophoresis. Its structure is:

```
AATTCGAGCTCGGTACCCGGGGATCCTCTAGAGTCGACCTGCAGCTG
    GCTCGAGCCATGGGCCCCTAGGAGATCTCAGCTGGACGTCGAC

TTGACAATTAATCATCGGCTCGTATAATGTGTGGAATTGTGAGCG
AACTGTTAATTAGTAGCCGAGCATATTACACACCTTAACACTCGC

GATAACAATTTCACACATAACGAGGCGCAAAAA
CTATTGTTAAAGTGTGTATTGCTCCGCGTTTTT

ATGAAAAAGACAGCTATCGCGATCGCAGTGGCACTGGCT
TACTTTTTCTGTCGATAGCGCTAGCGTCACCGTGACCGA

GGTTTCGCTACCGTAGCGCAGGCCAGC
CCAAAGCGATGGCATCGCGTCCGGTCG

GGTAAA
CCATTTTCGA
```

The insert DNA corresponding to Group Ab is excised by cutting the DNA with restriction endonucleases EcoRI and HindIII and is purified by polyacrylamide gel electrophoresis. Its structure is:

```
AATTCGAGCTCGGTACCCGGGGATCCTCTA
    GCTCGAGCCATGGGCCCCTAGGAGAT

GAGTCGACCTGCAGCTGTTGACAATTAATC
CTCAGCTGGACGTCGACAACTGTTAATTAG

ATCGGCTCGTATAATGTGTGGAATTGTGAG
TAGCCGAGCATATTACACACCTTAACACTC

CGGATAACAATTTCACACATAACGAGGCGC
GCCTATTGTTAAAGTGTGTATTGCTCCGCG

AAAAAATGAAAAAGACAGCTATCGCGATCGG
TTTTTTACTTTTTCTGTCGATAGCGCTAGCC

AGTGTAAGAAATGAGCGGTAAA
TCACATTCTTTACTCGCCATTTTCGA
```

The insert DNA corresponding to Group B is excised by cutting the DNA with restriction endonucleases HindIII and BamHI and is purified by polyacrylamide gel electrophoresis. Its structure is:

```
AGCTTCAAAGCTGGCGTATGCCCGCCG
    AGTTTCGACCGCATACGGGCGGC

AAAAAATCCGCGCAGTGTCTGCGGTACAAA
TTTTTTAGGCGCGTCACAGACGCCATGTTT

AAACCGGAATGCCAGTCCGACTGGCAGTGC
TTTGGCCTTACGGTCAGGCTGACCGTCACG

CCGGGTAAAAAACGTTGTTGCCCGGACACC
GGCCCATTTTTTGCAACAACGGGCCTGTGG

TGCGGCATCAAATGCCTG
ACGCCGTAGTTTACGGACCTAG
```

The insert DNA corresponding to Group C is excised by cutting the DNA with restriction endonucleoases BamHI and BglII and is purified by polyacrylamide gel electrophoresis. Its structure is:

```
GATCCGGTTGATACCCCGAACCCGACT
    GCCAACTATGGGGCTTGGGCTGA

CGTCGAAAACCGGGTAAATGCCCGGTA
GCAGCTTTTGGCCCATTTACGGGCCAT

ACCTATGGCCAGTGTCTGATGCTGAACCCG
TGGATACCGGTCACAGACTACGACTTGGGC
```

-continued
```
CCGAACTTCTGCGAAATGGACGGCCAGTGT
GGCTTGAAGACGCTTTACCTGCCGGTCACA

AAACGA
TTTGCTCTAG
```

The insert DNA corresponding to Group D is excised by cutting the DNA with restriction endonucleases SauIIIA and SalI and is purified by acrylamide gel electrophoresis. Its structure is:

```
GATCTGAAATGCTGTATGGGTATG
    ACTTTACGACATACCCATAC

TGCGGCAAATCTTGTGTTTCCCCG
ACGCCGTTTAGAACACAAAGGGGC

GTAAAAGCATAAG
CATTTTCGTATTCAGCT
```

B. Construction of the Gene

In the construction for export, the inserts from group Aa, B, C, and D are combined and ligated to M13 mp18 and 19 cut with EcoRI and SalI using T4 DNA ligases under standard conditions. The clones containing the gene are selected by their color on Xgal plates and screened further by hybridization with the $^{32}$P labelled oligonucleotide. The structure of selected clones is confirmed by dideoxy sequencing of the insert region of the DNA using the universal primer.

In the construction for cytoplasmic expression, the inserts from groups Ab, B, C, and D are combined and ligated to M13 mp18 and 19 cut with EcoRI and SalI using T4 DNA ligase under standard conditions. The clones containing the genes are selected by their color on Xgal plates and screened further by hybridization with the $^{32}$P labelled insert. The structures of selected clones are confirmed by dideoxy sequencing of the insert region of the DNA using the universal primer.

EXAMPLE 2

On the basis of the amino acid sequence described above, the codon usage in highly expressed genes of Escherichia coli, and the provision of convenient restriction endonuclease cleavage sites, the following DNA sequence was proposed:

To regulate the expression of the protein in a form such that the protein remains in the E. coli cytoplasm, the following operational elements are proposed: the tac promoter on plasmid pKK223-3; the lac operator of plasmid pKK223-3 and the lac repressor (lac I$^q$) on the chromosome of E. coli strain JM107; a consensus Shine-Dalgarno sequence; and, to initiate a high level of translation, a

```
                    HindIII
5' TCT GGT AAA AGC TTC AAA GCT GGC GTA TGC CCG CCG
                    AluI FnuDII                 RsaI              HpaII
AAA AAA TCC GCG CAG TGT CTG CGG TAC AAA AAA CCG
              HhAI XmaI
GAA TGC CAG TCC GAC TGG CAG TGC CCG GGT AAA AAA
                                     HpaII
                                     NciI HpaII
CGT TGT TGC CCG GAC ACC TGC GGC ATC AAA TGC CTG
              NciI         Fnu4HI              BstNI BamHI
GAT CCG GTT GAT ACC CCG AAC CCG ACT CGT CGA AAA
    HpaII                                  TaqI HpaII       HpaII           BalI
CCG GGT AAA TGC CCG GTA ACC TAT GGC CAG TGT CTG
NciI         NciI               HaeIII ATG CTG AAC CCG CCG AAC TTC TGC GAA ATG GAC GGC
                                              HaeIII BglII
CAG TGT AAA CGA GAT CTG AAA TGC TGT ATG GGT ATG
                MboI Fnu4HI                  NciI
TGC GGC AAA TCT TGT GTT TCC CCG GTA AAA GCA TAA 3'
                              HpaII
```

To regulate the expression of the protein in a form suitable for export to the periplasm of E. coli, the following regulatory elements are proposed: a tac promoter on plasmid pKK223-3 for initiation of transcription at high levels; a lac operator on plasmid pKK223-3 for transcription regulation; a lac repressor (lac I$^q$), to be encoded on the chromosome of E. coli strain JM107; an OmpA Shine-Dalgarno sequence to initiate translation at a high level; an OmpA leader to facilitate periplasmic export of the product; an Ala of an Ala-Ser junction between the protein sequence encoded by these operator elements and that encoded by the structural genes described above to dictate cleavage of the initial product to yield the mature leukocyte elastase inhibitor. The ompA elements are incorporated into the following DNA sequence:

fragment of the OmpA leader peptide to be used as a translational coupler. The translational coupling sequence comprises the DNA coding for the translation initiation region of the OmpA gene, the first eight amino acids of the OmpA leader peptide, the consensus Shine-Dalgarno sequence described above and a translational terminator. The translational coupling sequence is to be inserted between the lac operator and the translation initiation site of the serine protease inhibitor gene, overlapping the latter. The features of the translational coupler are incorporated into the following DNA sequence:

| GAATT | CGATA | TCTCG | TTGGA | GATAT | TCAT  | GACGT | ATTTT | GGATG | ATAAC | GAGGC |
| GCAAA | AAATG | AAAAA | GACAG | CTATC | GCGAT | CGCAG | TGGCA |       |       |       |
| CTGGC | TGGTT | TCGCT | ACCGT | AGCGC | AGGCC.|       |       |       |       |       |

| GAATT | CGATA | TCTCG | TTGGA | GATAT | TTCAT | GACGT | ATTTT | GGATG | ATAAC | GAGGC |
| GCAAA | AAATG | AAAAA | GACAG | CTATC | GCGAT | CAAGG | AGAAA | TAAAT | G. | |

C. Construction of Gene Fragments

To construct the above sequences, the following deoxyribonucleotides are synthesized using the ABI DNA synthesizer (Foster City, Calif.). The products are purified by polyacrylamide gel electrophoresis as described in the ABI instrument manual. They are 5' phosphorylated using T4 polynucleotide kinase and ATP using standard means.

The following group of oligonucleotide sequences are used to construct fragment Aa.

Oligonucleotide Aa1 is:
AATTCGATATCTCGTTGGAGATATTCATGACGTATTTTGGATGATAACGAGGCGCAAAA.

Oligonucleotide Aa2 is:
ATGAAAAAGACAGCTATCGCGATCG.

Oligonucleotide Aa3 is:
GATCCGATCGCGATAGCTGTCTTTTTCATTTTTGC.

Oligonucleotide Aa4 is:
GCCTCGTTATCATCCAAAATACGTCATGAATATCTCCAACGAGATATCG.

Oligonucleotide Aa5 is:
GATCCGATCGCAGTGGCACTGGCTGGTTTCGCTACCGTAGCGCAGGCCTCTGGTAAA.

Oligonucleotide Aa6 is:
AGCTTTTACCAGAGGCCTGCGCTACGGTAGCGAAACCAGCCAGTGCCACTGCGATCG.

The following oligonucleotide sequences are assembled to make up fragment Ab.

Oligonucleotide Ab1 is:
AATTCGATATCTCGTTGGAGATATTCATGACGTATTTTGGATGATAACGAGGCGCAAAA.

Oligonucleotide Ab2 is:
ATGAAAAAGACAGCTATCGCGATCG.

Oligonucleotide Ab3 is:
GATCCGATCGCGATAGCTGTCTTTTTCATTTTTGC.

Oligonucleotide Ab4 is:
GCCTCGTTATCATCCAAAATACGTCATGAATATCTCCAACGAGATATCG.

Oligonucleotide Ab5 is:
CAAGGAGAAATAAATGAGCGGTAAA.

Oligonucleotide Ab6 is:
AGCTTTTACCGCTCATTTATTTCTCCTTGAT.

The following are the oligonucleotide sequences assembled to construct fragment B.

Oligonucleotide B1 is:
AGCTT CAAAG CTGGC GTATG CCCGC CGAAA AAATC CGCG.

Oligonucleotide B2 is:
CAGTG TCTGC GGTAC AAAAA ACCGG AATGC CAG.

Oligonucleotide B3 is:
TCCGA CTGGC AGTGC CCGGG TAAAA AACGT TGTTG C.

Oligonucleotide B4 is:
CCGGA CACCT GCGGC ATCAA ATGCC TG.

Oligonucleotide B5 is:
GATCC AGGCA TTTGA TGCCG CAGGT GTCCG GCAA CAACG TTTTT TACCC GGGCA.

Oligonucleotide B6 is:
CTGCC AGTCG GACTG GCATT CCGGT TTTTT GTACC G.

Oligonucleotide B7 is:
CAGAC ACTGC GCGGA TTTTT TCGGC GGGCA TACGC CAGCT TGA.

The following are the oligonucleotide sequences used to construct fragment C.

Oligonucleotide C1 is:
GATCC GGTTG ATACC CCGAA CCCG.

Oligonucleotide C2 is:
ACTCG TCGAA AA.

Oligonucleotide C3 is:
CCGGG TAAAT GCCCG GTAAC CTATG GC.

Oligonucleotide C4 is:
CAGTG TCTGA TGCTG AACCC GCCGA AC.

Oligonucleotide C5 is:
TTCTG CGAAA TGGAC GGCCA GTGTA AACGA GAT.

Oligonucleotide C6 is:
CTAGA TCTCG TTTAC ACTGG CCGTC CATTT CGCAG AAGTT.

Oligonucleotide C7 is:
CGGCG GGTTC AGCAT CAGAC ACTGG CCATA GGTTA CCGGG CA.

Oligonucleotide C8 is:
TTTAC CCGGT TTTCG ACGAG TCGGG TT.

Oligonucleotide C9 is:
CGGGG TATCA ACCG.

The following group of oligonucleotide sequences are assembled to form fragment D.

Oligonucleotide D1 is:
GATCT GAAAT GCTGT ATGGG TATGT GCGGC.

Oligonucleotide D2 is:
AAATC TTGTG TTTCC CCGGT AAAAG CATAA G.

Oligonucleotide D3 is:
TCGAC TTATG CTTTT ACCGG GAAAA CACAA GATTT GCCGC A.

Oligonucleotide D4 is:
CATAC CCATA CAGCA TTTCA.

The following groups of oligonucleotides are mixed and annealed under standard conditions and ligated to each other and to cloning and sequencing vectors M13 mp18 and 19 cut with appropriate restriction endonucleases using T4 DNA ligase under standard conditions. The products are used to transform E. coli JM105 and clones containing the DNA of interest are selected by hybridization with $^{32}$P labelled oligonucleotides selected from the group used in the annealing step. The insert structure is confirmed by dideoxy sequencing of the cloned DNA using a universal primer.

Oligonucleotides Aa1–Aa4 are ligated to M13mp18 and M13mp19 cut with EcoRI and BamHI. M13 replicative form DNA having the desired insert DNA is recovered by standard means. The insert DNA is excised from the M13 DNA by cutting the M13 DNA with restriction endonucleases EcoRI and PvuI and is purified by polyacrylamide gel electrophoresis. Its structure is:

AATTCGATATCTCGTTGGAGATATTCATGACGTATTTTGGATGATAACGAGGCGCAAAAAATGA

GCTATAGAGCAACCTCTATAAGTACTGCATAAAACCTACTATTGCTCCGCGTTTTTTACT

AAAAGACAGCTATCGCGAT

TTTTCTGTCGATAGCGC

Oligonucleotides Aa5 and Aa6 are ligated to M13mp18 and m13mp19 cut with BamHI and HindIII. M13 replicative form DNA having the desired insert DNA is recovered by standard means. The insert DNA is excised from the M13 DNA by cutting the DNA with restriction endonucleases PvuI and HindIII and is purified by polyacrylamide gel electrophoresis. Its structure is:

Oligonucleotides Ab1–Ab4 are ligated to M13mp18 and M13mp19 cut with EcoRI and BamHI. M13 replicative form DNA having the desired insert DNA is recovered by standard means. The insert DNA is excised from the M13 DNA by cutting the DNA with restriction endonucleases EcoRI and PvuI and is purified by polyacrylamide gel electrophoresis. Its structure is:

CGCAGTGGCACTGGCTGGTTTCGCTACCGTAGCGCAGGCCTCTGGTAAA

TAGCGTCACCGTGACCGACCAAAGCGATGGCATCGCGTCCGGAGACCATTTTCGA

This PvuI-HindIII fragment is combined with the EcoRI-PvuI fragment prepared from oligonucleotides Aa1–Aa4 and ligated with M13mp18 or M13mp19 cut with EcoRI and HindIII. M13 replicative form DNA having the desired insert DNA is recovered by standard means. The insert DNA, which is DNA Fragment Aa, is excised from the M13 DNA by cutting the M13 DNA with restriction endonucleases EcoRI and HindIII and is purified by polyacrylamide gel electrophoresis. Its structure is:

AATTCGATATCTCGTTGGAGATATTCATGACGTATTTTGGATGATAACGAGGCGCAAAAAATGA

GCTATAGAGCAACCTCTATAAGTACTGCATAAAACCTACTATTGCTCCGCGTTTTTTACT

AAAAGACAGCTATCGCGATCGCAGTGGCACTGGCTGGTTTCGCTACCGTAGCGCAGGCCTCTGGT

TTTTCTGTCGATAGCGCTAGCGTCACCGTGACCGACCAAAGCGATGGCATCGCGTCCGGAGACCA

AA

TTTCGA

AATTCGATATCTCGTTGGAGATATTCATGACGTATTTTGGATGATAACGAGGCGCAAAAAATGA

GCTATAGAGCAACCTCTATAAGTACTGCATAAAACCTACTATTGCTCCGCGTTTTTTACT

AAAAGACAGCTATCGCGAT

TTTTCTGTCGATAGCGC

This EcoRI-PvuI fragment is combined with oligonucleotides Ab5 and Ab6 and ligated with M13mp18 or M13mp19 cut with EcoRI and HindIII. M13 replicative form DNA having the desired insert DNA is recovered by standard means. The insert DNA which is Fragment Ab is excised from the M13 DNA by cutting the DNA with restriction endonucleases EcoRI and HindIII and is purified by polyacrylamide gel electophoresis. Its structure is:

```
AATTCGATATCTCGTTGGAGATATTCATGACGTATTTTGGATGATAACGAGGCGCAAAAAATGA
    GCTATAGAGCAACCTCTATAAGTACTGCATAAAACCTACTATTGCTCCGCGTTTTTTACT
AAAAGACAGCTATCGCGATCAAGGAGAAATAAATGAGCGGTAAA
TTTTCTGTCGATAGCGCTAGTTCCTCTTTATTTACTCGCCATTTTCGA
```

Group B, which contains oligonucleotides B1 to B7, is ligated to M13mp 18 and 19 cut with HindIII and BamHI. The insert DNA corresponding to Group B is excised by cutting the DNA with restriction endonucleases HindIII and BamHI and is purified by polyacrylamide gel electrophoresis. Its structure is:

```
AGCTTCAAAGCTGGCGTATGCCCGCCG
    AGTTTCGACCGCATACGGGCGGC
AAAAAATCCGCGCAGTGTCTGCGGTACAAA
TTTTTTAGGCGCGTCACAGACGCCATGTTT
AAACCGGAATGCCAGTCCGACTGGCAGTGC
TTTGGCCTTACGGTCAGGCTGACCGTCACG
CCGGGTAAAAAACGTTGTTGCCCGGACACC
GGCCCATTTTTTGCAACAACGGGCCTGTGG
TGCGGCATCAAATGCCTG
ACGCCGTAGTTTACGGACCTAG
```

Group C, which contains oligonucleotides C1 to C9, is ligated to M13mp 18 and 19 cut with BamHI and XbaI. The insert DNA corresponding to Group C is excised by cutting the DNA with restriction endonucleoases BamHI and BglII and is purified by polyacrylamide gel electrophoresis. Its structure is:

```
GATCCGGTTGATACCCCGAACCCGACT
    GCCAACTATGGGGCTTGGGCTGA
CGTCGAAAACCGGGTAAATGCCCGGTA
GCAGCTTTTGGCCCATTTACGGGCCAT
ACCTATGGCCAGTGTCTGATGCTGAACCCG
TGGATACCGGTCACAGACTACGACTTGGGC
CCGAACTTCTGCGAAATGGACGGCCAGTGT
GGCTTGAAGACGCTTTACCTGCCGGTCACA
AAACGA
TTTGCTCTAG
```

Group D, which contains oligonucleotides D1 to D4, is ligated to M13mp 18 and 19 cut with BamHI and SalI. The insert DNA corresponding to Group D is excised by cutting the DNA with restriction endonucleases SauIIIA and SalI and is purified by acrylamide gel electrophoresis. Its structure is:

```
GATCTGAAATGCTGTATGGGTATG
    ACTTTACGACATACCCATAC
TGCGGCAAATCTTGTGTTTCCCCG
ACGCCGTTTAGAACACAAAGGGGC
GTAAAAGCATAAG
CATTTTCGTATTCAGCT
```

D. Construction of the Gene

In the construction for export, the inserts from Groups Aa, B, C, and D are combined and ligated to M13 mp18 and 19 cut with EcoRI and SalI using T4 DNA ligase under standard conditions. In the construction for cytoplasmic expression, the inserts from Groups Ab, B, C and D are combined and ligated to M13 mp18 and 19 cut with EcoRI and SalI using T4 DNA ligase under standard conditions. The clones containing the gene are selected by their color on Xgal plates and screened further by hybridization with the $^{32}$P labelled oligonucleotide. The structure of selected clones is confirmed by dideoxy sequencing of the insert region of the DNA using the universal primer.

EXAMPLE 3

Construction of Expression Vectors

The inserts for the construction for export and the construction for cytoplasmic expression were transferred to expression plasmids as follows. M13 replicative form DNA having the desired insert DNA is recovered by standard means as indicated above. The appropriate insert DNA is excised from the M13 DNA by cutting the DNA with restriction endonucleases EcoRI and PstI and is purified by polyacrylamide gel electrophoresis. It is then ligated to pKK223-3 cut with restriction endonucleases EcoRI and PstI and the resulting plasmid cloned into E. coli JM107. The construction for use in Examples 4 and 5 for export is pSGE6 and that for use in Example 7 for cytoplasmic expression is pSGE8. The E. coli strain for export in Examples 4 and 5 is SGE10 and that for cytoplasmic expression in Example 6 is SGE30.

A. Organization of pSGE6

Plasmid pSGE6 was constructed by replacing the DNA between the EcoRl and PstI sites of pKK223-3 with an EcoRI/PstI fragment containing DNA coding for ompA SLPI. The DNA sequence of ompA-SLPI is as follows:

```
            10         20         30         40         50         60
       GAATTCGATA TCTCGTTGGA GATATTCATG ACGTATTTTG GATGATAACG AGGCGCAAAA
       CTTAAGCTAT AGAGCAACCT CTATAAGTAC TGCATAAAAC CTACTATTGC TCCGCGTTTT 70         80         90        100        110        120
       AATGAAAAAG ACAGCTATCG CGATCGCAGT GGCACTGGCT GGTTTCGCTA CCGTAGCGCA
       TTACTTTTTC TGTCGATAGC GCTAGCGTCA CCGTGACCBA CCAAAGCGAT GGCATCGCGT 130        140        150        160        170        180
       GGCCTCTGGT AAAAGCTTCA AAGCTGGCGT ATGCCCGCCG AAAAAATCCG CGCAGTGTCT
       CCGGAGACCA TTTTCGAAGT TTCGACCGCA TACGGGCGGC TTTTTTAGGC GCGTCACAGA 190        200        210        220        230        240
       GCGGTACAAA AAACCGGAAT GCCAGTCCGA CTGGCAGTGC CCGGGTAAAA AACGTTGTTG
       CGCCATGTTT TTTGGCCTTA CGGTCAGGCT GACCGTCACG GGCCCATTTT TTGCAACAAC 250        260        270        280        290        300
       CCCGGACACC TGCGGCATCA AATGCCTGGA TCCGGTTGAT ACCCCGAACC CGACTCGTCG
       GGGCCTGTGG ACGCCGTAGT TTACGGACCT AGGCCAACTA TGGGGCTTGG GCTGAGCAGC 310        320        330        340        350        360
       AAAACCGGGT AAATGCCCGG TAACCTATGG CCAGTGTCTG ATGCTGAACC CGCCGAACTT
       TTTTGGCCCA TTTACGGGCC ATTGGATACC GGTCACAGAC TACGACTTGG GCGGCTTGAA 370        380        390        400        410        420
       CTGCGAAATG GACGGCCAGT GTAAACGAGA TCTGAAATGC TGTATGGGTA TGTGCGGCAA
       GACGCTTTAC CTGCCGGTCA CATTTGCTCT AGACTTTACG ACATACCCAT ACACGCCGTT 430        440        450        460
       ATCTTGTGTT TCCCCGGTAA AAGCATAAGT CGACCTGCAG
       TAGAACACAA AGGGGCCATT TTCGTATTCA GCTGGACGTC
```

The sequence hereinafter referred to as "ompA-SLPI" is the DNA from the final M13mp18 construct for export discussed above. Plasmid pSGE6 is depicted in FIG. 1. In FIG. 1, the first codon for ompAss-SLPI is at position 62–64 of the DNA sequence called "ompA-SLPI." The first codon for mature SLPI is at position 125–127. Ptac contains DNA for the tac promoter, lac operator and the beta galactosidase Shine/Dalgarno sequence. The abbreviations Rl, Pst and Bam are recognition sequences for the restriction enzymes EcoRI, PstI and BamHI. Tet® is a part of the gene from pBR322 which confers resistance to tetracycline, amp® confers resistance to ampicillin, rrnB contains the DNA from the rrnB operon from position 6416 to position 6840. Arrows indicate the direction of transcription.

B. Organization of pCJ-ompA-SLPI

Plasmid pCJ-ompA-SLPI is the same as pSGE6 except that it contains the complete tetracycline resistance gene and promoter rather than the partial gene. This plasmid confers tetracycline resistance when inserted into *E. coli* and was constructed in a analogous fashion to pSGE6 except that the EcoRI/PstI fragment containing DNA coding for ompA SLPI was cloned into vector pCJ1 rather than pKK223-3. The vector pCJ1 was constructed as follows. Plasmid pKK223-3 was digested completely with SphI and partially with BamHI. A 4.4 Kbp fragment was gel purified and combined with a synthetic adaptor:

```
GATCTAGAATTGTCATGTTTGACAGCTTATCAT

ATCTTAACAGTACAAACTGTCGAATAGTAGC
``` and a 539 bp fragment of DNA from a ClaI, SphI digest of the tet® gene of pBR322 (PL Biochemicals, 27-4891-01).

C. Structure of pSGE8

Figure 2:
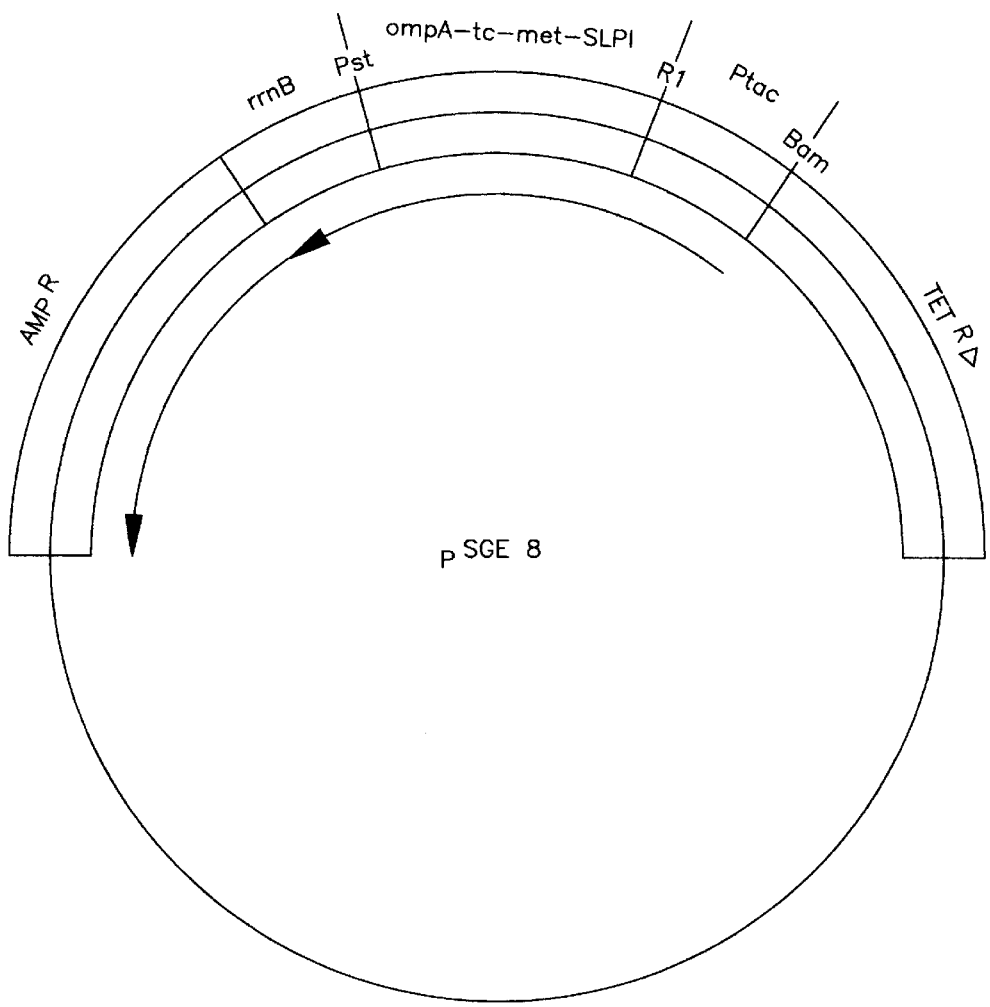
FIG. 2 is a map of plasmid pSGE8.

Plasmid pSGE8 is isogenic to pSGE6 with the exception that the DNA between the EcoRI and Pst sites contains the sequence called ompA-tc-met-SLPI which is derived from the final M13mp18 construct for cytoplasmic expression as discussed above. This sequence directs the synthesis of methionyl-SLPI in the cytoplasm of *E. coli*. A partial diagram of pSGE8 is contained in FIG. 2. In the sequence called "ompA-tc-met-SLPI," the initiation codon for ompA is at position 62–64, the termination codon is at 95–97, and the initiation codon for methionyl-SLPI is at 98–100. The DNA sequence of ompA-tc-met-SLPI is as follows:

```
            10         20         30         40         50         60
       GAATTCGATA TCTCGTTGGA GATATTCATG ACGTATTTTG GATGATAACG AGGCGCAAAA

CTTAAGCTAT AGAGCAACCT CTATAAGTAC TGCATAAAAC CTACTATTGC TCCGCGTTTT 70         80         90        100        110        120
       AATGAAAAAG ACAGCTATCG CGATCAAGGA GAAATAAATG AGCGGTAAAA GCTTCAAAGC

TTACTTTTTC TCTCGATAGC GCTAGTTCCT CTTTATTTAC TCGCCATTTT CGAAGTTTCG 130        140        150        160        170        180
       TGGCGTATGC CCGCCGAAAA AATCCGCGCA GTGTCTGCGG TACAAAAAAC CGGAATGCCA

ACCGCATACG GGCGGCTTTT TTAGGCGCGT CACAGACGCC ATGTTTTTTG GCCTTACGGT
```

-continued

```
          190        200        210        220        230        240
    GTCCGACTGG CAGTGCCCGG GTAAAAAACG TTGTTGCCCG GACACCTGCG GCATCAAATG

CAGGCTGACC GTCACGGGCC CATTTTTTGC AACAACGGGC CTGTGGACGC CGTAGTTTAC 250        260        270        280        290        300
    CCTGGATCCG GTTGATACCC CGAACCCGAC TCGTCGAAAA CCGGGTAAAT GCCCGGTAAC

GGACCTAGGC CAACTATGGG GCTTGGGCTG AGCAGCTTTT GGCCCATTTA CGGGCCATTG 310        320        330        340        350        360
    CTATGGCCAG TGTCTGATGC TGAACCCGCC GAACTTCTGC GAAATGGACG GCCAGTGTAA

GATACCGGTC ACAGACTACG ACTTGGGCGG CTTGAAGACG CTTTACCTGC CGGTCACATT 370        380        390        400        410        420
    ACGAGATCTG AAATGCTGTA TGGGTATGTG CGGCAAATCT TGTGTTTCCC CGGTAAAAGC

TGCTCTAGAC TTTACGACAT ACCCATACAC GCCGTTTAGA ACACAAAGGG GCCATTTTCG
```

D. Organization of pCJ-met-SLPI

Plasmid pCJ-met-SLPI is the same as pSGE8 except that it contains the complete (rather than the partial) tetracycline resistance gene. Plasmid CJ-met-SLPI was constructed analogously to pSGE8 except that the EcoRI/PstI fragment containing DNA coding for ompA-tc-met-SLPI was cloned into vector pCJ1 rather than pKK223-3.

E. Construction of Yeast Expression Plasmids

The plasmid pUC8 was digested with HindIII and ligated to a HindIII/SmaI adaptor (obtained from Amersham, Cat. No. DA1006). The addition of this adaptor to a HindIII site does not reconstruct the HindIII site. The DNA was then digested with SmaI and ligated in dilute solution followed by tranformation of E. coli JM83. The correct plasmid, i.e., a plasmid lacking the restriction sites in the polylinker from the HindIII site to the SmaI site, was identified by digesting plasmid DNA isolated from transformants with EcoRI, SmaI or HindIII. A transformant containing a plasmid that lacked the HindIII site but contained the EcoRI site and SmaI site was identified in this manner. This plasmid is pGS185.

Figure 3:
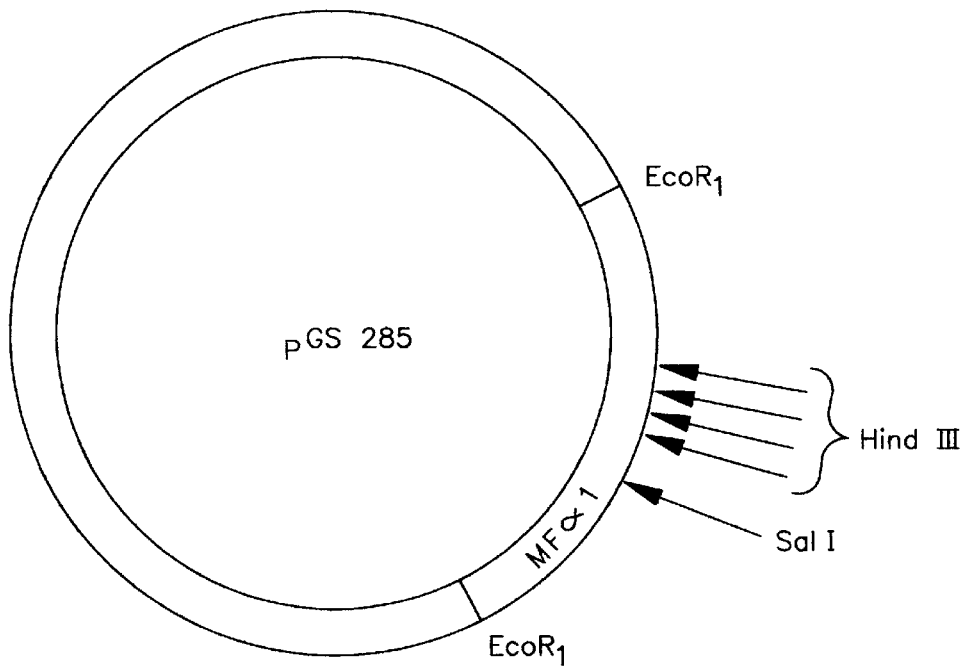
FIG. 3 is a map of plasmid pGS285.

An EcoRI fragment containing the yeast MFα1 gene was purified by gel electrophoresis from the plasmid pCY17 as described by J. Kurjan & I. Herskowitz in Cell 30:933 (1982), specifically incorporated herein by reference, and ligated into EcoRI cut pGS185. This ligation mixture was used to transform E. coli HB101, selecting for ampicillin resistance. Plasmid DNA was isolated from transformants and the presence of the correct insert confirmed by digests of the DNA with EcoRI. This is plasmid pGS285 and is depicted in FIG. 3.

Plasmid pGS285 was digested to completion with HindIII and religated under dilute conditions to eliminate three of the four internal HindIII sites in the MFα1 gene as noted by Kurjan & Herskowitz, ibid. The correct construct was selcted as described above. This is plasmid pGS385.

The M13 AaBCD clone as described in Example 2 that carries nucleotide sequences encoding amino acids four through 107 of the synthetic SLPI gene, was digested with HindIII. This DNA was ligated with the following oligonucleotide adaptor:

5' GCT GAA GCT TCA GGT AAG CGA CTT CGA AGT CCA TTC TCGA.

This adaptor had been formed by annealing the two oligonucleotides:

5' GCT GAA GCT TCA GGT AAG and 5' AGC TCT TAC CTG AAG CTT CAGC first at 70° C. for 2' followed by slow cooling overnight.

Figure 4:
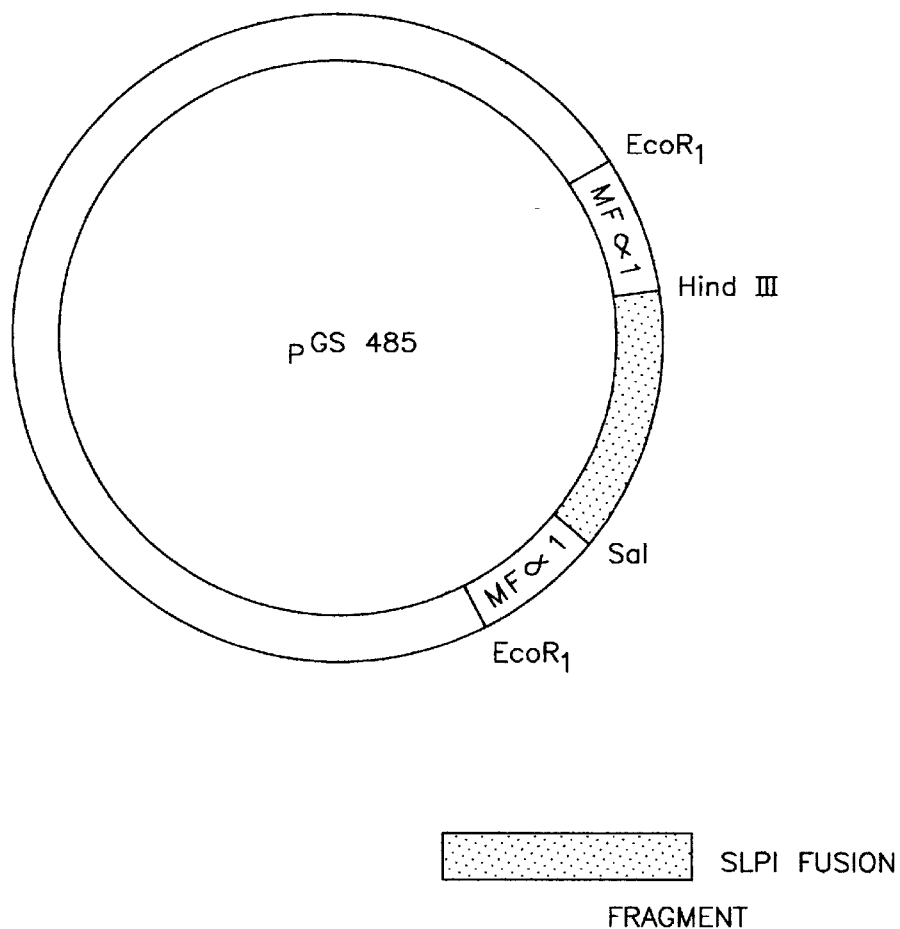
FIG. 4 is a map of plasmid pGS485.
Figure 5:
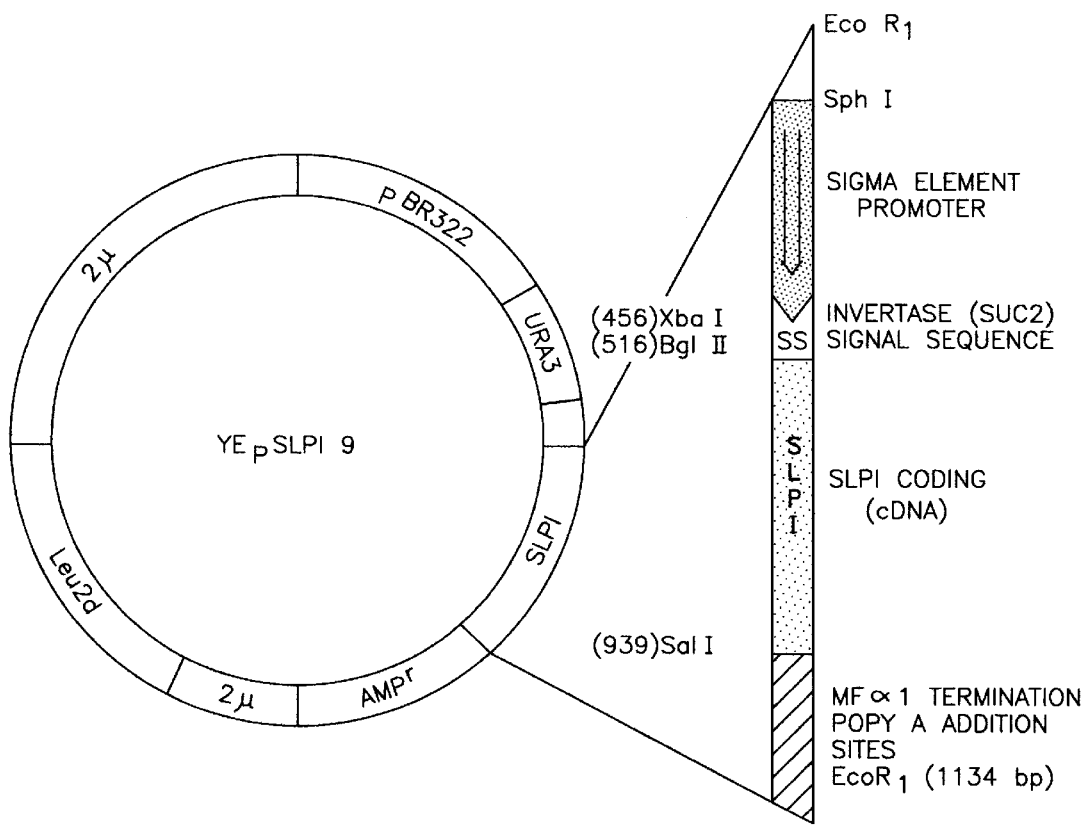
FIG. 5 is a map of plasmid YEpSLPI-9.

Following ligation of the adaptor to HindIII cut M13 AaBCD, the ligation mix was digested with HindIII and SalI to release a fragment purified by agarose gel electrophoresis and electrolution. This fragment was digested once more with HindIII and then ligated with pGS385 DNA that had been cut with HindIII and SalI. E. coli HB101 was transformed with the ligation mixture and ampicillin resistant transformants were selected. Transformants containing plasmids with the correct insert DNA were identified by preparing plasmid DNA and digesting it with HindIII and SalI. A plasmid constructed and isolated in this manner has been designated pGS485 and is depicted in FIG. 4. This plasmid contains the MFα1 gene fused, in frame, to the synthetic SLPI gene at the HindIII site in the first spacer region of the MFα1 gene. Such constructs, when placed in yeast, have been demonstrated to direct the synthesis, processing and secretion of the heterologous proteins as shown by A. J. Brake et al. in PNAS (USA) 81:4642, specifically incorporated herein by reference. The fusion of the MFα1 gene and SLPI is contained on an EcoRI fragment in pGS485. This EcoRl fragment was cloned into the vector YIp5 as described in Example 8.

EXAMPLE 4

Expression and purification of secretory leukocyte protease inhibitor (SLPI) using plasmid pSGE6.

E. coli cells containing plasmid pSGE6 (SGE10 cells) were cultured for 6 hours in 10 liters of M9 media with 2% tryptone, 0.5% yeast extract, 20 g/l glucose, 200 mg/l Vitamin $B_1$ and 100 mg/l ampicillin added. IPTG was added to 0.2 mM and the culture grown for another 6 hours. Ten liters of E. coli SGE10 cells, at 8 grams per liter, were pelleted at 18,000×g and resuspended in 50 mM Tris.HCl (pH 7.5), 4 mM EDTA buffer (hereinafter T50E4) and pelleted. The pellet was resuspended in 2.7 liters T50E4 and frozen in 150 ml lots. Eight of these lots (equivalent to 36 gms of cells) were pooled and lysed by a single pass through a french press at 12,000 psi and 4° C. The lysate was centrifuged for 1.5 hrs at 20,000×g. One sixth of the pellet containing the cell insolubles (equivalent to six grams of cells) was washed twice with 125 ml of T50E4 and the remaining material was frozen overnight.

The frozen pellet was extracted with 25 ml of 100 mM Tris.HCl (pH 8.0), 4 mM EDTA (hereinafter T100E4) containing 20 mM DTT (obtained from Sigma, Cat. No. D-0632), 4 mM PMSF (obtained from Sigma, Cat. No. P-7626) and 8M urea (ultrapure, obtained from BRL, Cat. No. 5505UA) for 1 hr at 37° C. and centrifuged at 10,000×g for ten minutes. The resultant supernatant was mixed with 10 ml packed Sephadex SP-C25 (obtained from Pharmacia)

which had been pre-equilibrated with the extraction buffer T100E4 containing 20 mM DTT and 8M urea and mixed on a roller for ten minutes at 37° C. to absorb the SLPI to the SP-Sephadex.

The resin with the absorbed SLPI was pelleted by a ten minute centrifuge at 3,000×g and the supernatant decanted. The remaining resin was washed twice with 25 ml of T100E4 containing 20 mM DTT and 8M urea followed by two washes with 25 ml T100E4 containing 20 mM DTT. The resin was then extracted once with a mixture of 0.6 ml 5M NaCl and 25 ml of T100E4 containing 20 mM DTT and 0.3M NaCl. This extract contained about 0.15 mg/ml protein and more than 0.04 mg/ml SLPI. The SLPI obtained by this method was determined to be greater than 70% pure by high pressure liquid chromatography.

EXAMPLE 5

Using the method of Example 4, a second frozen pellet was extracted with T100E4 containing 1% Triton x-100 (obtained from Sigma, Cat. No. T-6878) in place of the first T100E4/DTT/PMSF/urea wash. The resultant SLPI was slightly more pure than that obtained in Example 4 and gave higher activity in the refolding assay set forth in Example 6 below.

EXAMPLE 6

Refolding purified SLPI.

About 40 ug of partially-purified SLPI from Example 4 or 5 was made 8M in urea or 5M in guanidine hydrochloride (obtained from Pierce Chemical Co., #24110), and 4 mM in DTT and incubated for 1 hr at room temperature. Oxidized glutathione (obtained from Sigma, Cat. No. G-4626) was added to 13.5 mM and the mixture was again incubated for 1 hr at room temperature. The mixture was diluted 10-fold with a solution of 50 mM Tris in NaOH, pH10.7 and incubated for a further 4 hrs at room temp. The mixture was then diluted 5-fold with 50 mM Tris, pH8.0, and 0.15M NaCl and applied to a 1×2 cm column of Sepahdex SP-C25 preequilibrated with 50 mM Tris, pH8.0 and 0.25M NaCl. The resin was washed with 50 mM Tris, pH 8.0, containing 0.25M NaCl and then with 50 mM Tris, pH8.0, containing 0.5M NaCl. The fraction eluting with the 0.5M salt wash was fully active and represented about 30% of the SLPI applied to the column.

EXAMPLE 7

Purification of SLPI from soluble and insoluble fractions of SGE30 cell lysate.

Expression of the plasmid pSGE8 in *E. coli* SGE30 cells produced SLPI in both the soluble and insoluble fractions of the cell lysate. At 1% of the total cell protein, the SLPI was distributed about 80% to the soluble and about 20% to the insoluble fractions.

A. Purification of SLPI from the insoluble fraction

The *E. coli* SGE30 cells containing pSGE8 were grown in LB Media containing 50 ug/ml ampicillin in a shaker flask to an OD600 of 0.7 and induced by the addition of IPTG to 0.2 mM. After three hours the cells are pelleted and were suspended in two times their weight of 50 mM Tris.HCl (pH 7.5) and 4 mM EDTA (hereinafter T50E4). The cells were disrupted by sonication at 4° C. and the extract was centrifuged for 20 minutes at 4° C. at 12,000×g.

The pellet was washed in three volumes of T50E4 and was solublized at room temperature in a solution containing either 10M urea or 6M guanidine hydrochloride, and 5 mM reduced DTT. After a one hour incubation at room temperature, oxidized glutathione was added at a concentration of 17.5 mM and the mixture was incubated for another hour. The mixture was then diluted into 10 volumes of 50 mM Tris.HCl, pH 10.7. The diluted mixture was allowed to stand for 4 hours at room temperature followed by pH adjustment to 8 by the addition of 5N HCl. This mixture was centrifuged to remove precipitated protein.

The supernatant so produced contained SLPI which exhibited secretory leukocyte protease inhibitor activity. This protein was purified by chromatography on a Sephadex SP-C25 column as described above.

B. Purification of SLPI from soluble fraction

*E. coli* pSGE30 cells containing plasmid pSGE8 were grown in a shaker flask to an OD600 of 0.7 and induced by the addition of IPTG to 0.2 mM. At an OD600 of 1.1, the cells were pelleted at 25,000×g for 15 minutes. The pellet was resuspended in T50E4 and was lysed by two passages through a french press at 20,000 psi at 4° C. The lysate was centrifuged at 25,000×g for 15 minutes.

The supernatant was made 25 mM in DTT. This mixture was incubated at 0° C. for one hour and sufficient HCl was added to reach a final concentration of 5%. After a 30 minute incubation at 0° C., the mixture was centrifuged at 25,000×g for 15 minutes and the supernatant removed for further processing. The pH of the supernatant was adjusted to 8.0 with 10M NaOH and analyzed by SDS-PAGE, reverse phase hplc chromatography and ELISA which indicated at least 0.7 ug SLPI per 130 ug total protein. The SLPI thus obtained was further purified on a Sephadex SP-C25 chromatography column. It was refolded to active SLPI according to Example 6.

EXAMPLE 8

The EcoRl fragment containing the fused SLPI-MFα1 gene (see Ex. 3.E.) was ligated to the EcoRI site of the yeast vector YIp5 as described by D. Botstein and R. W. Davis in *The Molecular Biology of the Yeast Saccharomyces,* Cold Spring Harbor Laboratory, pp. 607–636 (1982), specifically incorporated herein by reference, to generate YIpSLPI-1 and has been integrated into the URA3 gene of *S. cerevisiae* BS214 (MATα, Ura3-52, pep4, prb1) by site-directed recombination as described by T. Orr-Weaver et al. in Methods in Enzymology 101:228 (1983), specifically incorporated herein by reference. This strain, *S. cerevisiae* SGY-1, secretes fully active SLPI into the culture supernate.

A second strain, SGY-3, also produces and secretes active SLPI. This strain carries the MFα1::SLPI fusion on the replicating yeast plasmid pGS585. This plasmid was constructed from pJDB207 as described by J. R. Broach in Methods in Enzymology 101:307 (1983), specifically incorporated herein by reference, by the addition of the yeast URA3 gene, isolated from the plasmid YEp24 as described by D. Botstein and R. W. Davis in *The Molecular Biology of the Yeast Saccharomyces,* Cold Spring Harbor Laboratory, pp. 607–636, specifically incorporated herein by reference, and cloned into the HindIII site of pJDB207 to construct pGS585. The MFα1::SLPI fusion gene, contained on an EcoRI fragment, was cloned into the SalI site of pGS585 using EcoRI-XhoI adaptors (obtained from Amersham, Cat. No. DA1007) to generate YEpSLPI-1. This plasmid was introduced into *S. cerevisiae* DBY746 (MATα, Ura3-52, leu2-3, his3 1, trp 1-289) by transformation as described by Ito et al. in J. Bacteriology 153:163 (1983), specifically incorporated herein by reference.

*Saccharomyces cerevisiae* strains SGY-1 and SGY-3 were grown at 30° C. to stationary phase in SD medium lacking uracil according to the method of F. Sherman et al. described in *Methods in Yeast Genetics,* p. 62, Cold Spring Harbor Laboratories, Cold Spring Harbor, New York (1981), specifically incorporated herein by reference. Cells were removed from the culture medium by centrifugation and the culture supernatant was assayed for SLPI activity by measuring (1) protease inhibitory activity and (2) the amount of material that specifically reacts with anti-SLPI antibodies by an enzyme-linked immunoassay. Purification schemes may be developed in a manner analogous to prior methods described herein.

EXAMPLE 9

Construction and Expression of a Secretory Leukocyte Protease Inhibitor (SLPI) Analog that has Chymotrypsin and Elastase Inhibitory Activity An analog of SLPI has been constructed in which the first 72 amino acids of the primary translation product of the SLPI gene have been deleted. This deletion removes the signal sequence and the first 47 amino acids of the mature protein. The protein expressed from this altered gene is 60 amino acids long and inhibits chymotrypsin and elastase, but not trypsin.

The amino acid sequence of this molecule as expressed in yeast and the nucleotide sequence of the corresponding cDNA clone for this analog are as follows:

```
CTG GAT CCT GTT GAC ACC CCA ACA CCA ACA AGG AGG AAG
 L   D   P   V   D   T   P   N   P   T   R   R   K

CCT GGG AAG TGC CCA GTG ACT TAT GGC CAA TGT TTG ATG
 L   G   K   C   P   V   T   Y   G   Q   C   L   M

CTT AAC CCC CCC AAT TTC TGT GAG ATG GAT GGC CAG TGC
 L   N   P   P   N   F   C   E   M   D   G   Q   C

AAG CGT GAC TTG AAG TGC TGC ATG GGC ATG TGT GGG AAA
 K   R   D   L   K   C   C   M   G   M   C   G   K

TCC TGC GTT TCC CCT GTG AAA GCT TGA
 S   C   V   S   P   V   K   A   END
```

There are several potential advantages to this analog of SLPI. First, there may be situations in which the presence of the trypsin inhibitory domain is detrimental to the use of SLPI as a pharmacologic agent. Second, if this analog is as active as SLPI on a per-molecule basis, it would allow one to administer a smaller dose and perhaps decrease production costs. Third, the observation that the first domain is not essential to the correct folding and activity of the second domain, raises the possibility that one could substitute another peptide sequence for the trypsin inhibitor region generating a novel protein with additional activities, specificities, stability, or target sites. Finally, the results suggest that even smaller derivatives of SLPI with the desired activity are possible.

Construction and Expression of an SLPI Analog

The deletion of the trypsin inhibitory domain was made by digesting the SLPI cDNA clone, designated cSLPI-I and deposited under ATCC Accession No. 40207, with BamHI and EcoRI. The approximately 370 base pair BamHI-EcoRI fragment representing the 3' portion of the cDNA was gel purified and recut with AluI. An AluI to SalI adaptor

```
CCTGATAAGCCGACTGATAAG
GGACTATTCGGGCTGACTATTCAGCT
``` was synthesized and ligated to this fragment. The ligation mixture was then digested with BamHI, to release multimers joined at the BamHI site, and SalI to remove multimers of the adaptor. The resulting BamHI SalI fragment was gel purified and ligated to BamHI and SalI digested pBR322 DNA. This plasmid (pGS786-3) was cloned in *E. coli* HB101. pGS786-3 was then digested with HindIII and BamHI and the pBR322 DNA between these two sites was replaced with the HindIII-BamHI adaptor

```
AGCTTGGATAAGAGATTG
    ACCTATTCTCTAACCTAG
``` to create the plasmid pGS986-2. The coding region of SLPI in pGS986-2 is contained on a HindIII-SalI fragment that allows an in frame fusion to the pre-pro sequence of MFαH gene.

The HindIII-SalI fragment of pGS986-2 was gel purified and cloned into HindIII, SalI cut MF H (contained in pGS186). The plasmid isolated from these reactions has been designated pGS1086 and consists of the last 60 codons of the SLPI cDNA clone fused to the MFαH gene. The alpha-factor/domain II fusion is contained on a 1.7 KB EcoRI fragment, that also contains the alpha-factor promoter, transcriptional termination signals and polyadenylation site. The EcoRI fragment containing the gene fusion was gel purified, EcoRI to XhoI adaptors added and cloned into the SalI site of pGS585. The plasmid, pGS585, contains the 2 micron circle origin of replication, the Leu2d gene and the URA3 gene, as well as sequences derived from pBR322. Transcription of the SLPI DNA is in the direction of the URA3 gene.

This plasmid was used to transform *S. cerevisiae* DBY746 CIR°-5. URA3+ transformants were selected and assayed for the extracellular production of an active chymotrypsin inhibitor. One isolate, SGY10, has been characterized and is secreting approximately 1 microgram per ml of an active chymotrypsin inhibitor. This inhibitor was purified by chromatography on an anhydrochymotrypsin affinity column, followed by HPLC on a C8 column and the material was sequenced. Seven amino acid residues were determined and the sequence indicates that the inhibitor is derived from SLPI and is accurately processed by *S. cerevisae*. The modified version of SLPI begins with the sequence LEU-ASP-PRO-VAL-ASP-THR-PRO. As expected, expression of the second domain of SLPI results in an inhibitor with anti-chymotrypsin activity but no detectable activity toward trypsin.

EXAMPLE 10

This example describes the production of authentic, active human SLPI in the yeast *Saccharomyces cerevisiae*. Also described is a method for the purification of this protein from yeast. The functional elements of this recombinant system utilize a yeast episomal vector containing the complete 2μ plasmid of yeast with the Leu2, as described by (J. D. Beggs in Nature 275:104, and Ura 3, as described by Rose et al. in Gene 29:113, genes of *S. cerevisiae* for use as selectable markers in yeast and an *E. coli* replicon with the ampicillin resistance gene for selection in *E. coli*. Both the Beggs and Rose et al. articles are specifically incorporated herein by reference. A strong yeast promoter that is regulated by the two yeast peptide mating factors (Stetler and Thorner in Proc. Natl. Acad. Sci. 81:1144, specifically incorporated herein by reference) was utilized to direct transcription of SLPI fused to a synthetic secretory signal sequence. Transcriptional terminator sequences and polyadenylation signals were provided by a fragment of the MFα1 gene of *S. cerevisiae* described by Kurjan and Hershowitz in Cell 30:933, specifically incorporated herein by reference. When this construct is carried in yeast cells of mating type a and transcription is induced by the addition of mating factor α, SLPI is synthesized, the signal sequence processed, and the mature polypeptide transported to a cellular or extracellular compartment from which it is readily extracted by low concentrations of Triton X 100 in the presence of high concentrations of sodium chloride. The protein extracted by this method is readily purified by established methods, it is correctly processed, is fully active, and it reacts with antibody produced to the native, human protein.

CONSTRUCTION OF THE PLASMID YEpSLPI-9

Unless specifically stated otherwise, the following conditions were used throughout: restriction endonuclease digests were done with 20 units of enzyme per microgram of DNA in the buffer recommended by the manufacturer for at least two hours; enzymes were inactivated and removed by the addition of sodium EDTA to a final concentration of 15 mM and heated at 70° C. for 30 minutes, and the sample was then ethanol precipitated; ethanol precipitations were carried out by the addition of ammonium acetate to 2.5M followed by the addition of two volumes of 100% ethanol. DNA was pelleted from this solution without cooling by centrifugation at 12,000×g for 10 minutes. The precipitated DNA was mixed with 80% ethanol and reprecipitated by centrifugation at 12,000×g for 5 minutes. This step was followed by mixing the DNA pellet with 100% ethanol and centrifuging at 12,000×g for 5 minutes, the ethanol removed, and the precipitated DNA dried in vacuuo. All oligonucleotides were synthesized on an Applied Biosystems DNA synthesizer and were purified as previously described in EXAMPLE 1. *E. coli* transformations were done as described by Maniatis et al., *Molecular Cloning* p. 249, Cold Spring Harbor Laboratory New York (1982), specifically incorporated herein by reference. Plasmid DNA was prepared by the alkaline SDS method, and agarose and acrylamide gel electrophoresis was carried out essentially as described by Maniatis et al., supra. DNA fragments were purified by electrophoresis through polyacrylamide gels as was described by Maniatis et al., supra. DNA fragments were purified from agarose gels by using FMC SeaPlaque agarose, low melting point (LMP) and Schleicher & Schuell Elutip-d columns as described in Schleicher & Schuell Technical Bulletin #206.

Construction of pGS185

The first step in the assembly of YEpSLPI-9 required the construction of a plasmid with an EcoRI site but lacking a HindIII site. To do this, the plasmid pUC8 DNA (Bethesda Research Labs, BRL) was digested with HindIII and ethanol precipitated and the dry precipitate was dissolved in 11 ul of water. This DNA was ligated to a HindIII-SmaI adaptor (PL Biochemicals #7488; a phosphorylated HindIII-SmaI adaptor which does not recreate the HindIII site). The ligation was carried out in a final volume of 20 ul as follows:

| | | |
|---|---|---|
| 1.5 ug | HindIII cut pUC8 DNA | |
| 1.0 ug | phosphorylated HindIII—SmaI adaptor DNA | |
| 2 units | T4 DNA ligase (BRL) | |
| 2 ul | 10X ligase buffer (Maniatis et al., supra) | |
| final volume = 20 ul | | | final volume=20 ul

The ligation mixture was incubated at 4° C. for 16 hours then ethanol precipitated. The precipitated DNA was next digested with SmaI endonuclease, ethanol precipitated, and dissolved in 10 ul of water. The plasmid was recircularized in the following reaction:

| | |
|---|---|
| 10 ul | SmaI cut DNA |
| 5 ul | 10X ligase buffer |
| 33 ul | $H_2O$ |
| 2 ul | 2 units T4 DNA ligase (BRL) |

The ligation mixture was incubated at 4° C. for 16 hours. The *E. coli* strain JM83 was transformed with 5 ul of the reaction mixture and ampicillin resistant colonies were selected. Twelve colony isolates were used to prepare individual 1.5 ml cultures in LB-ampicillin broth and plasmid DNA was prepared therefrom. 0.2 ug samples of plasmid DNA from each of the 12 isolates were digested with HindIII and analyzed by agarose gel electrophoresis. Eleven of the 12 isolates did not cut with HindIII. DNA from one of these 11 isolates was further analyzed by digestion with EcoRI and SmaI endonucleases and on this basis the plasmid was shown to contain both an EcoRI site and a SmaI site. This plasmid has been designated pGS185.

Construction of Plasmid pGS286

A 100 ml culture of *E. coli* carrying the plasmid pGS185 was used to prepare plasmid DNA. The MFαH gene (a modification of the MFα1 gene described by Kurjan and Hershowitz, supra) containing an additional HindIII site at nucleotide 1200 (with the 5' proximal EcoRI site serving as nucleotide #1) was isolated from pUC9 MFαH by digesting 8 ug of plasmid DNA with EcoRI. The digested DNA was electrophoresed in a 5.0% polyacrylamide gel and the 1.7 kb EcoRI fragment containing the MFαH gene purified therefrom. The MFαH EcoRI fragment was ligated to EcoRI cut pGS185 as follows:

45 ng MFαH DNA
15 ng EcoRI-digested pGS185 DNA
2 ul 10× ligase buffer
2 units DNA ligase (BRL)

The final volume was adjusted to 20 ul with $H_2O$.

The reaction mixture was incubated 2 hours at 37° C. and *E. coli* strain JM83 was transformed with 5 ul of the ligation mixture. Ampicillin resistant colonies were screened by hybridization (Maniatis et al., supra) with a $^{32}$P-labeled DNA fragment (Maniatis et al., supra). Eight colonies that produced hybridization signals were grown and used to prepare plasmid DNA and the presence of the MFαH gene in these isolates was verified by HindIII or EcoRI digests followed by gel electrophoresis. Three of the eight, hybridization positive isolates contained a DNA fragment with the expected MFαH gene restriction sites.

Replacement of the MFαH Promotor with a Polylinker

Ten micrograms of plasmid pGS286 DNA was digested with XbaI and PstI endonucleases, and the large plasmid fragment of interest was purified away from the smaller DNA fragments by electrophoreses in a 0.7% LMP agarose gel. The following two oligonucleotides were synthesized and purified:

```
MFP
           10         20         30         40         50
5'-CTAGGCATGC TTTCTAGACC CGGGATTAAA ACCATGAGAT TTCCTTCAAT
           60
TTTCACTGCA-3'

MFPL
           10         20         30         40         50
5'-GTGAAAATTG AAGGAAATCT CATGGTTTTA ATCCCGGGTC TAGAAAGCAT GC-3'
```

Two micrograms of MFP and MFPL were dried under vacuum and dissolved in 10 ul of 10 mM Tris, pH 8.0; 1 mM EDTA buffer (TE buffer). The 5' end of the duplex contains an end that can be ligated to an XbaI site without regeneration of that site, while the 3' end can be ligated to a PstI site with regeneration of that site. The duplex also contains internal SphI, XbaI, and SmaI sites. The non-phosphorylated MFP/MFPL duplex was ligated to XbaI and PstI digested, gel purified pGS286 plasmid DNA as follows.

| | |
|---|---|
| 0.5 ug | Xba-PstI digested pGS286 DNA |
| 1.0 ug | MFP/MFPL duplex |
| 1 ug | 10X ligase buffer |
| 1 ul | 1 unit T4 DNA ligase (BRL) |

Water was added to reach a final volume of 10 ul.

The ligation mixture was incubated 16 hours at 4° C., and E. coli DH5 was transformed with 1 ul of the ligation mixture. Ampicillin resistant transformants were selected and grown, and diagnostic restriction digests on the DNA purified therefrom were carried out with the restriction enzymes XbaI and SphI. One transformant containing a plasmid with the expected restriction sites was isolated and designated pGS286 pa. This construct deletes approximately 963 nucleotides 5' to and including the translational initiation site, and substitutes a 60 basepair (bp) adaptor that recreates the initiator methionine of MFαH, and introduces three new restriction sites. This construct does not possess a functional promoter.

Removal of the BglII Site from pGS286 pa

Because the synthetic invertase signal sequence (described in detail below) utilizes an internal BglII site, it was necessary to remove the BglII site present at nucleotide 40 in the MFαH sequence. To do this, the following ligation was done.

| | |
|---|---|
| 1 ug | BglII digested pGS286 Δ pa DNA |
| 1 ug | EcoRI—XhoI—BamHI adaptor (Amersham #DA1007) |
| 4 ug | 5X ligase buffer (BRL) |
| 2 ul | 2 units T4 DNA ligase (BRL) |

Water is added to reach a final volume of 20 ul.

The ligation mixture was incubated at 23° C. for 60 minutes and then the following was added:

| | |
|---|---|
| 8 ul | XhoI buffer |
| 5 ul | 50 units XhoI |
| 67 ul | H$_2$O |

This reaction mixture was incubated at 37° C. for 2 hours then ethanol precipitated. The XhoI digested, ethanol precipitated ligation mixture was religated under dilute conditions at 23° C. for 60 minutes as follows:

| | |
|---|---|
| 20 ul | 5X ligase buffer |
| 5 ul | 5 units T4 DNA ligase (BRL) |
| 75 ul | H$_2$O |

One microliter of this ligation mixture was used to transform E. coli DH5. Ampicillin resistant colonies were selected. A correct construct would contain an XhoI site, but would lack the prior BglII site (ligation of a BamHI end to a BglII end would not recreate either site). Transformants containing plasmids of this description were identified by diagnostic restriction digests on plasmid DNA purified from the individual isolates using XhoI, BglII, or BamHI endonucleases. A transformant cell carrying the correct plasmid DNA was identified and labeled pGS286 pa BglII.

Construction of a Plasmid Containing the Synthetic Invertase Signal Sequence Fused to a Fragment of the SLPI cDNA Clone The amino acid sequence of the invertase signal sequence is: MMLLQAFLFLLAGFAAKISA as described by M. E. Watson in NAR 12:5145, specifically incorporated herein by reference. Reverse translation of this protein sequence to the corresponding nucleotide sequence demonstrated that it was possible to produce a DNA sequence that would include several useful restriction sites which would also allow fusion of this sequence to SLPI or to other proteins of interest. For this reason, the following two oligonucleotides were synthesized:

2186A

```
        XbaI      10              20              30              40              50
5'-CTAGAACCAT  GATGCTTTTG  CAGGCCTTCC  TTTTCCTTTT  GGCTGGTTTT
          60  BglII      70
GCAGCCAAGA  TCTCTGCAGT  AC-3'
```

2186B

```
              10              20              30              40              50
5'-TGCAGAGATC  TTGGCTGCAA  AACCAGCCAA  AAGGAAAAGG  AAGGCCTGCA
          60
AAAGCATCAT  GGTT-3'
```

Oligo nucleotide 2186A (1.6 ug) and oligonucleotide 2186B (1.6 ug) were mixed and dried under vacuum. To the dry pellet, the following components were added:

| | |
|---|---|
| 23.5 ul | H₂O |
| 3.0 ul | medium salt buffer |
| 3.0 ul | 30 units BglII |
| 0.5 ul | 0.1 M spermidine, pH 7.0 |
| 23.5 ul | H₂O |

The reaction mix was incubated at 37° C. for 2 hours followed by an ethanol precipitation.

The following adaptor oligonucleotides were also synthesized.

2586A

```
              10              20              30
5'-GATCTCTGCA  TCTGGTAAGT  CTTTCAAGGC  TGG-3'
```

2586B

```
              10              20              30
5'-ACTCCAGCCT  TGAAAGACTT  ACCAGATGCA  GA
```

When 2586A and 2586B were hybridized to form a duplex, they generated a double-stranded adaptor with a 5' BglII compatible end and a 3' HinfI compatible end. This adaptor allows fusion of the SLPI cDNA sequence to the invertase leader.

The 2586 A+B duplex (3.2 ug) was ligated with the BglII digested 2186 A+B duplex in the following reaction mixture for 16 hours at 4° C.

| | |
|---|---|
| 6 ul | ligase buffer (BRL) |
| 2 ul | 2 units T4 DNA ligase (BRL) |
| 22 ul | H₂O |

Note that none of the oligonucleotides in this reaction were phosphorylated in vitro, however, the BglII digestion of 2186 A+B DNA generated the necessary 5' phosphate to allow the ligation of the two oligonucleotide pairs at the BglII site. The absence of phosphates from the XbaI terminus of the 2186 pair and the HinfI terminus of the 2586 pair prevented end-to-end ligation. The expected product from this ligation is a 96 bp adaptor with a 5' XbaI end and a 3' HinfI end. This 96 bp adaptor (SUC2-SLPI) was purified by 6% acrylamide gel electrophoresis. Plasmid pGS286 pa BglII (5 ug) was digested to completion with XbaI and SalI endonucleases. The XbaI-SalI cut plasmid DNA was purified by electrophoresis in 0.7% agarose gel from the 700 bp fragment containing the alpha factor coding region. The SLPI cDNA clone contained in pUC19 as an EcoRI fragment, was used to generate the next series of plasmids. Ten micrograms of the pCSLPI plasmid DNA was digested with EcoRI and HindIII, and the 390 bp fragment containing the coding region of SLPI was purified by electrophoresis in a 5% polyacrylamide gel. The fragment was subcloned into EcoRI and HindIII cut pBR322 DNA as follows:

| | | |
|---|---|---|
| 0.2 | ug | EcoRI—HindIII cut pBR322 DNA |
| 0.075 | ug | 390 bp cSLPI EcoRI, HindIII fragment |
| 2 | ul | 10X ligase buffer |
| 1 | unit | T4 DNA ligase (BRL) |
| | | H₂O to 20 ul |

The ligation mixture was incubated at room temperature for 2 hours and *E. coli* HB101 was transformed with 3 ul of the ligation mixture, and ampicillin resistant transformants were selected. Plasmid DNA was prepared from twelve isolates and checked for the presence of the cSLPI insert by digestion with HindIII and EcoRI endonucleases followed by analysis on a 5% acrylamide gel. All twelve isolates contained the expected DNA fragment as determined by size. One of these isolates was selected for further use, it was called pGS586.

Plasmid pGS586 DNA (20 ug) was digested with HindIII and SalI endonucleases and purified by gel electrophoresis in 0.7% LMP agarose. A pair of oligonucleotides (986 and 1086) bps were synthesized to recreate the final codon of SLPI in order to provide translational termination signals and restriction sites which would allow fusion to MFα1, MFαH, or to pGS286 pa BglII.

```
             HindIII                    SalI 986      5'-AGCTTGATAAGCCCGAG-3'

1086      3'-ACTATTCGGGCTCAGCT-5'
```

Oligonucleotides 986 (0.5 ug) and 1086 (0.5 ug) were kinased in a final volume of 20 ul containing 10 units of T4 polynucleotide kinase; (New England Biolabs) 0.066M Tris-HCl, pH 7.5; 1 mM ATP; 1 mM spermidine; 0.01M MgCl₂; and 3.3 mM dithiothreitol (K/L buffer). The kinased adaptors were added to the HindIII-SalI digested and gel purified pGS586 plasmid DNA in the following reaction:

| | | |
|---|---|---|
| 0.25 | ug | HindIII—SalI digested pGS586 DNA |
| 0.64 | ug | kinased adaptor 986/1086 |
| 1.00 | ug | 10X K/L buffer |
| 1 | unit | T4 DNA ligase (BRL) |
| | | H₂O to 10 ul |

The ligation reaction was incubated at 16° C. for 3 hours. The mixture was then diluted with 14 ul of water, and NaCl was added to a final concentration of 0.1M, along with 50 units of SalI; incubation was continued at 37° C. for 2 additional hours followed by ethanol precipitation. The precipitated DNA was taken up in:

| 220 ul  | H₂O                |
|---------|--------------------|
| 25 ul   | 10X K/L buffer     |
| 5 units | T4 DNA ligase (BRL)|

The incubation was continued for 1 hour at 23° C. *E. coli* HB101 was transformed with 50 ul of the final ligation mixture and transformants were selected by plating the transformed cells on media containing ampicillin. Ninety transformants selected in this manner were screened by colony hybridization (Maniatis et al., supra at 312) using the $^{32}$P-labeled 986 oligonucleotide. The reaction was carried out as follows:

| 10 pM | oligonucleotide 986    |
|-------|------------------------|
| 20 pM | -$^{32}$ATP 5000 Ci/mMole | in a reaction mixtue of:

| 8 ul | H₂O                                      |
|------|------------------------------------------|
| 1 ul | 10X kinase buffer                        |
| 1 ul | 10 units T4 kinase (New England Biolabs) |

The filters were hybridized in a standard hybridization solution (Maniatis et al., supra) without formamide at 42° C. for 20 hours. The filters were washed in 5× SSC (Maniatis et al., supra), and 1% SDS at 52° C. for 60 minutes. Eighty-seven of the ninety transformants hybridized to the probe. The structure of three of these isolates was confirmed by direct, dideoxy sequencing, as described by Sanger and Coulson in J. Mol. Biol. 94:441, specifically incorporated herein by reference of the plasmid described by Chen and Seeburg in DNA 4:165, specifically incorporated herein by reference. The sequencing utilized the following primer.

5'-CGACGATAGTCATGCCCCGCGC-3'

Use of this primer allows one to sequence counterclockwise from the SalI site in pBR322 directly into the HindIII-SalI adaptor. Two of the three sequenced isolates had the correct structure, and one was selected for further use, it was named pGS686.

Ten micrograms of pGS686 DNA was digested with EcoRI and SalI endonucleases. The EcoRI to SalI fragment was purified by electrophoresis in a 5% polyacrylamide gel. The EcoRI to SalI fragment was further digested with HinfI and then ethanol precipitated. The HinfI-SalI fragment which contains the SLPI coding information was fused to the invertase signal sequence and cloned into XbaI-SalI digested pGS286 pa BglII DNA in the following reaction:

| 0.1  | ug  | XbaI—SalI digested, gel purified pGS286 Δ pa Δ BglII DNA |
| 0.02 | ug  | XbaI—HinfI digested, non-phosphorylated, gel-purified SUC2-SLPI adaptor DNA |
| 0.1  | ug  | HinfI—SalI digested cSLPI fragment |
| 3    | ul  | 5x ligase buffer (BRL)              |
| 1    | ul  | 1 unit T4 DNA ligase (BRL)          |
|      |     | H₂O to 15 ul                        |

The ligation mixture was incubated at 4° C. for 16 hours and used to transform *E. coli* DH5. Ampicillin resistant colonies were selected. Plasmid DNA was prepared from 24 isolates and analyzed by digestion with StuI and SalI endonucleases followed by polyacrylamide gel electrophoresis. Three isolates were identified that contained the expected fragments. One was chosen for further use, it was called pSUC2.

Addition of a Promoter to pSUC2

Figure 6:
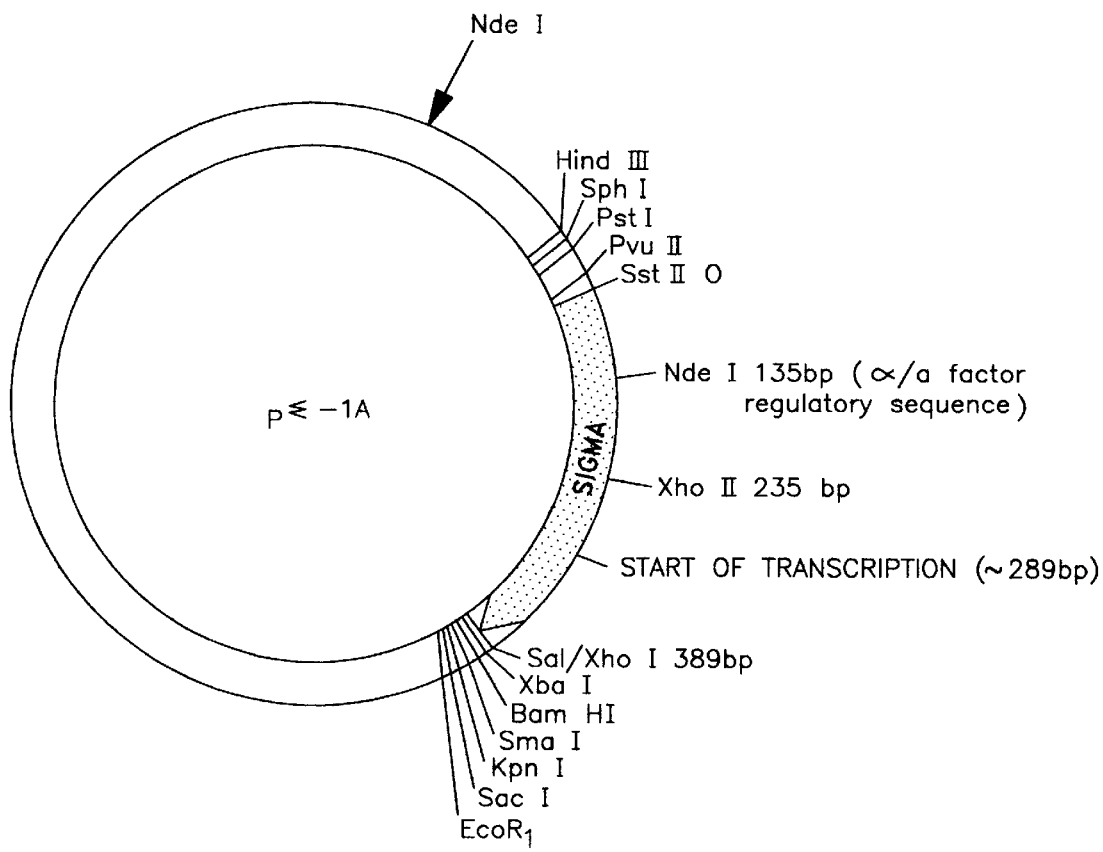
FIG. 6 is a map of plasmid pΣ-1A.

The mating factor regulated promoter α was isolated from the plasmid pΣ1A depicted in FIG. 6) by digestion with XbaI and SphI endonucleases. The promoter fragment was purified by LMP agarose electrophoresis as described above. The plasmid pSUC2 (5 ug) was also digested with XbaI and SphI then purified by LMP agarose electrophoresis. The sigma promoter was ligated to pSUC2 as follows:

| 0.1 ug |      | XbaI—SphI digested pSUC2 DNA |
| 0.1 ug |      | XbaI—SphI sigma fragment     |
| 2      | ul   | 5X ligase buffer (BRL)       |
| 1      | unit | T4 DNA ligase (BRL)          |
|        |      | H₂O to 10 ul                 |

The ligation mixture was incubated at 23° C. for 2 hours. A portion of the ligation mixture was used to transform *E. coli* strain DH5. Plasmid DNA was isolated from 12 transformants and analyzed by digestion with EcoRI endonuclease followed by agarose gel electrophoresis. Eight of the original 12 transformants contained EcoRI fragments of the correct size; one was chosen for further use and named pSUC2-6.

Subcloning into the Yeast Vector PC₁U

Fifty micrograms of plasmid pSUC2-6 DNA was digested to completion with EcoRI and the 1100 bp fragment containing the SUC2-SLPI fusion, the sigma promoter, and the MFα1 terminator/polyadenylation signals was purified by agarose gel electrophoresis. EcoRI-XhoI adaptors were added to this fragment as follows:

| 0.5 ug |    | 1100 bp EcoRI fragment                              |
| 1.0 ug |    | phosphorylated EcoRI—XhoI adaptor (Amersham #DA 1007) |
| 1.0 ul |    | 10X K/L buffer                                      |
| 2.0 ul |    | T4 DNA ligase (BRL)                                 |
|        |    | H₂O to 10 ul                                        |

The ligation mixture was incubated at 4° C. for 16 hours. Following the incubation, the reaction mixture was diluted to 120 ul in Xho-I restriction enzyme buffer and digested with XhoI endonuclease. The XhoI-adapted fragment was repurified by agarose gel electrophoresis. This fragment was subcloned into PC₁U as follows:

| 50 ng  |      | SalI digested PC₁U       |
| 250 ng |      | XhoI—adapted fragment    |
| 4      | ul   | 5X ligase buffer (BRL)   |
| 1      | unit | T4 DNA ligase (BRL)      |
|        |      | H₂O to 20 ul             |

The ligation was carried out at 23° C. for 3 hours, and *E. coli* DH5 was transformed with a portion of the ligation mixture. Transformants were selected by growth on media containing ampicillin. One hundred and fifty (150) transformants thus selected were screened by hybridization with $^{32}$P-labeled oligonucleotide 2186B (labeled with $^{32}$P-γATP and polynucleotide kinase). The hybridization was at 42° C. in 5× SSC; 50% formamide; 0.1% SDS; and 200 ug/ml yeast tRNA for 16 hours. Filters were washed for 60 minutes in five changes of 2× SSC, 1% SDS at 65° C., dried and exposed to x-ray film. Seventeen transformants hybridized with this probe, and twelve were chosen for restriction enzyme analysis. Plasmid DNA was prepared and digested with EcoRI, and the digests were analyzed by agarose gel electrophoresis. All twelve plasmids carried fragments of the correct size, and one, YEpSLPI-9, was chosen for further analysis. Plasmid YEpSLPI-9 is depicted in FIG. 6.

EXPRESSION OF SLPI IN S. CEREVISIAE DBY747cir°-1 TRANSFORMED WITH THE PLASMID YEpSLPI-9

S. cerevisiae DBy747cir°-1 was transformed with 2 ug of YEpSLPI-9 plasmid DNA by the method of Ito et al. set forth in J. Bact. 153:163, specifically incorporated herein by reference. Transformants were selected by plating on SD media, described by Sherman et al. in Methods in Yeast Genetics p. 62 (1981), specifically incorporated herein by reference, lacking uracil but otherwise containing all supplements necessary for growth of this strain (SD-Ura). All the transformants were found to produce material that crossreacted with antibody to SLPI. One strain, SGY15, was chosen for further study.

A culture of SGY15 grown in SD-uracil-leucine was grown to saturation (~5×10$^7$ cells/ml). This culture was diluted 20-fold into 300 ml of SD-leucine medium and incubated at 30° C., with shaking, until the cell number reached 2×10$^7$/ml. At that point, 12 ml of 10% glucose; 25 ml of 5% Difco casaminoacids; and 400 ug of alpha factor (Sigma) were added to the culture and incubated for an additional 4 hours at which point the cells were processed as follows:

1. The cells were collected by centrifugation at 5000 rpm in a Sorvall JA10 rotor for 5 minutes.
2. The cell pellet was resuspended in 25 ml of H$_2$O and the cells collected by centrifugation at 6000 rpm in a Sorvall JA20 rotor.
3. The cell pellet was resuspended in 5 ml of 0.25% Triton X100, 0.5M NaCl; and 10 mM sodium phosphate, pH 7.5 (TNN). The resuspended pellet was incubated at 37° C. for 60 minutes and the cells collected by centrifugation at 5000 rpm in a Sorvall JA20 rotor. The cell pellet was again resuspended in TNN and extracted as above for 60 minutes. This step was repeated a total of four times.
4. SLPI was quantitated in each extract by assaying its ability to inhibit alpha-chymotrypsin described by Thompson and Ohlsson in Proc. Natl. Acad. Sci. 83:6692, specifically incorporated herein by reference, with the following results.

| | |
|---|---|
| 60 minute extract | 35 ug SLPI |
| 120 minute extract | 105 ug SLPI |
| 180 minute extract | 51 ug SLPI |
| 240 minute extract | 25 ug SLPI |

The total SLPI recovered from the 300 ml culture was 216 ug.

5. The extracts were combined and chromatographed on a 0.6 ml anhydrochymotrypsin column as described previously. The extract was loaded on the column at a flow rate of 20 ml/hour and the column washed with 20 ml 10 mM Tris, pH 7.0. SLPI was eluted with 3.6 ml of 20 mM HCl.
6. One hundred micrograms of SLPI (quantitated by chymotrypsin inhibitory activity) was recovered.
7. This material was further purified by chromatography on a C-8 HPLC column as described previously. The sequence of nine amino terminal residues was determined using an Applied Biosystems gas phase sequentor. The sequence obtained confirms that the SLPI produced by SGY15 and extracted by the procedure outlined above is correctly processed from the SUC2 signal sequence.

It will be apparent to those skilled in the art that various modifications and variations can be made to the processes and products of the present invention. Thus, it is intended that the present invention cover the modifications and variations of this invention provided they come within the scope of the appended claims and their equivalents.

What is claimed is:

1. A DNA sequence encoding an analog of a mammalian serine protease inhibitor protein, said analog comprising at least eight cysteine residues and possessing serine protease inhibitor activity, wherein at least one active site comprises an amino acid sequence selected from the group consisting of amino acid sequences:

Gln-Cys-Leu-R$_2$-Tyr-Lys-Lys-Pro-Glu-Cys-Gln-Ser-Asp; and

Gln-Cys-R$_8$-R$_3$-R$_9$-Asn-Pro-Pro-Asn-Phe-Cys-Glu-R$_4$-Asp wherein

R$_2$, R$_3$ and R$_4$ are the same or different and are selected from the group consisting of methionine, valine, alanine, phenylalanine, tyrosine, tryptophan, lysine, glycine and arginine; and R$_8$ and R$_9$ are the same or different and are selected from the group consisting of methionine, valine, alanine, phenylalanine, tyrosine, tryptophan, lysine, glycine, leucine and arginine.

2. A DNA sequence according to claim 1, wherein R$_2$ and R$_3$ are methionine.

3. A DNA sequence according to claim 1, wherein R$_2$ and R$_3$ are arginine.

4. A DNA sequence according to claim 1, wherein R$_2$ is arginine and R$_3$ is methionine.

5. A DNA sequence according to claim 1, wherein R$_2$, R$_3$ and R$_4$ are methionine and R$_8$ and R$_9$ are leucine.

6. A DNA sequence according to claim 1, wherein one or more of R$_2$, R$_3$, R$_4$, R$_8$ or R$_9$ is valine.

7. A DNA sequence according to claim 1, wherein one or more of R$_2$, R$_3$, R$_4$, R$_8$ or R$_9$ is alanine.

8. A DNA sequence according to claim 1, wherein one or more of R$_2$, R$_3$, R$_4$, R$_8$ or R$_9$ is selected from a group consisting of phenylalanine, tyrosine and tryptophan.

9. A DNA sequence according to claim 1, wherein one or more of R$_2$, R$_3$, R$_4$, R$_8$ or R$_9$ is selected from the group consisting of lysine or arginine.

10. A host cell transformed or transfected with a DNA sequence according to claim 1.

11. A host cell according to claim 10, wherein said host cell is a microorganism.

12. A host cell according to claim 11, wherein said microorganism is selected from genera in the group consisting of Escherichia, Bacillus and Saccharomyces.

13. A method for producing a recombinant serine protease inhibitor protein analog possessing serine protease inhibitor activity, said method comprising the steps of:

(a) culturing a host cell transformed or transfected with a DNA sequence of claim 1 under conditions suitable for expression of the serine protease inhibitor protein analog, and;

(b) harvesting the serine protease inhibitor protein analog.

14. A method according to claim 13, wherein said host cell is a microorganism.

15. A method according to claim 13, wherein said microorganism is selected from genera in the group consisting of Escherichia, Bacillus and Saccharomyces.

16. A method according to claim 13, wherein $R_2$ and $R_3$ are methionine.

17. A method according to claim 13, wherein $R_2$ and $R_3$ are arginine.

18. A method according to claim 13, wherein $R_2$ is arginine and $R_3$ is methionine.

19. A method according to claim 13, wherein $R_2$, $R_3$ and $R_4$ are methionine and $R_8$ and $R_9$ are leucine.

20. A method according to claim 13, wherein one or more of $R_2$, $R_3$, $R_4$, $R_8$ or $R_9$ is valine.

21. A method according to claim 13, wherein one or more of $R_2$, $R_3$, $R_4$, $R_8$ or $R_9$ is alanine.

22. A method according to claim 13, wherein one or more of $R_2$, $R_3$, $R_4$, $R_8$ or $R_9$ is selected from a group consisting of phenylalanine, tyrosine and tryptophan.

23. A method according to claim 13, wherein one or more of $R_2$, $R_3$, $R_4$, $R_8$ or $R_9$ is selected from the group consisting of lysine or arginine.

* * * * *

UNITED STATES PATENT AND TRADEMARK OFFICE
CERTIFICATE OF CORRECTION

PATENT NO. : 5,871,956
DATED : February 16, 1999
INVENTOR(S) : Bandyopadhyay et al.

It is certified that error appears in the above-identified patent and that said Letters Patent is hereby corrected as shown below:

Title page,
Item [54] Title, add -- Protease -- after "Serine".
Item [63] Related U.S. Application Data, line 5, change "903,471, Sep 3, 1986," to -- 803,471, Dec 2, 1985, --.
Item [56] OTHER PUBLICATIONS, under "Julius et al.", change "Factor,3" to -- Factor," --.

Column 1,
Line 2, add -- Protease -- after "Serine".
Lines 11-12, change "06/903,471, filed Sep. 3, 1986," to -- 803,471 filed December 2, 1985, --.

Column 7,
Line 44, change "protein s" to -- proteins --.

Column 8,
Line 28, change "Asn Phe Cys Gly" to -- Asn Phe Cys Glu --.

Column 10,
Line 7, change "Leu to" to -- Leu to Ala --.

Column 11,
Line 1, add -- 3´ -- after "TAA".

Column 14,
Line 67, last line of sequence, replace the first "G" with -- T --.

Column 25,
Line 2, change "CGCAG" to -- CGGAG --.

Column 37,
Line 37, change "Tet®" to -- Tet$^r$ --.
Line 38, change "amp®" to -- amp$^r$ --.

Column 38,
Line 37, change "tet®" to -- tet$^r$ --.
Line 59, position 71, change "TCTCGATAGC" to -- TGTCGATAGC --.

Column 39,
Line 15, position 421, add -- ATAAGTCGAC CTGCAG TATTCAGCTG GACGTC --.
Line 53, change "selcted" to -- selected --.

UNITED STATES PATENT AND TRADEMARK OFFICE
CERTIFICATE OF CORRECTION

PATENT NO. : 5,871,956
DATED : February 16, 1999
INVENTOR(S) : Bandyopadhyay et al.

It is certified that error appears in the above-identified patent and that said Letters Patent is hereby corrected as shown below:

Column 42,
Line 14, change "pSGE30" to -- SGE30 --.

Column 43,
Line 33, change the first "L" under CCT to -- P --.
Line 38, change "AAG TGC" to -- AAG TGT --.

Column 44,
Line 1, change "CCTGATAAGCCGACTGATAAG" to -- CCTGATAAGCCCGACTGATAAG --.
Line 23, change "MF H" to -- MFαH --.

Column 47,
Lines 54 and 61, change "pGS286 pa" to -- pGS286 Δ pa Δ --.

Column 48,
Line 51, change "pa" to -- Δ pa Δ --.

Column 49,
Line 60, change "pa" to -- Δ pa Δ --.

Column 50,
Line 42, change "pa" to -- Δ pa Δ --.

Column 51,
Line 21, change "-$^{32}$ATP" to -- $\gamma^{32}$ATP --.

Signed and Sealed this

Twenty-sixth Day of February, 2002

*Attest:*

*Attesting Officer*

JAMES E. ROGAN
*Director of the United States Patent and Trademark Office*